(12) United States Patent
Stadtmueller et al.

(10) Patent No.: US 8,785,464 B2
(45) Date of Patent: Jul. 22, 2014

(54) PYRIMIDINE DERIVATIVES THAT INHIBIT FAK/PTK2

(71) Applicants: Heinz Stadtmueller, Vienna (AT); Bodo Betzemeier, Biberach an der Riss (DE); Ioannis Sapountzis, Gau-Algesheim (AT)

(72) Inventors: Heinz Stadtmueller, Vienna (AT); Bodo Betzemeier, Biberach an der Riss (DE); Ioannis Sapountzis, Gau-Algesheim (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/049,575

(22) Filed: Oct. 9, 2013

(65) Prior Publication Data

US 2014/0038993 A1    Feb. 6, 2014

Related U.S. Application Data

(63) Continuation of application No. 13/130,069, filed as application No. PCT/EP2009/065762 on Nov. 24, 2009, now abandoned.

(30) Foreign Application Priority Data

Nov. 24, 2008   (EP) .................................... 08169805

(51) Int. Cl.
   *C07D 401/12*   (2006.01)
   *C07D 401/14*   (2006.01)
   *A61K 31/505*   (2006.01)

(52) U.S. Cl.
   USPC ........... 514/269; 514/275; 544/320; 544/321; 544/330

(58) Field of Classification Search
   USPC .................. 544/320, 321, 330; 514/269, 275
   See application file for complete search history.

(56) References Cited

U.S. PATENT DOCUMENTS

| | | | |
|---|---|---|---|
| 7,173,028 B2 * | 2/2007 | Dahmann et al. .......... | 514/235.8 |
| 7,442,705 B2 | 10/2008 | Guillemont et al. | |
| 7,504,396 B2 | 3/2009 | Nunes et al. | |
| 7,521,457 B2 | 4/2009 | Stadtmueller et al. | |
| 7,569,561 B2 | 8/2009 | Stadtmueller et al. | |
| 7,585,870 B2 | 9/2009 | Guillemont et al. | |
| 2002/0137747 A1 | 9/2002 | Moriarty et al. | |
| 2005/0261295 A1 | 11/2005 | Stadtmueller et al. | |
| 2006/0148800 A1 | 7/2006 | Stadtmueller et al. | |
| 2007/0032514 A1 | 2/2007 | Zahn et al. | |
| 2008/0255172 A1 | 10/2008 | Su et al. | |
| 2011/0288071 A1 | 11/2011 | Stadtmueller et al. | |
| 2011/0288109 A1 | 11/2011 | Stadtmueller et al. | |
| 2012/0094999 A1 * | 4/2012 | Gray et al. ................. | 514/235.8 |

FOREIGN PATENT DOCUMENTS

| | | |
|---|---|---|
| EP | 1598343 | 11/2005 |
| WO | 9841512 A1 | 9/1998 |
| WO | 0012485 A1 | 3/2000 |
| WO | 0164653 A1 | 9/2001 |
| WO | 0164654 A1 | 9/2001 |
| WO | 0164655 A1 | 9/2001 |
| WO | 0204429 A1 | 1/2002 |
| WO | 2004048343 A1 | 6/2004 |
| WO | 2004074244 A2 | 9/2004 |
| WO | 2004080980 A1 | 9/2004 |
| WO | 2005016894 A1 | 2/2005 |
| WO | 2006021457 A2 | 3/2006 |
| WO | 2006035068 A2 | 4/2006 |
| WO | 2006076646 A2 | 7/2006 |
| WO | 2007003596 A1 | 1/2007 |
| WO | 2007035309 A1 | 3/2007 |
| WO | 2007096351 A1 | 8/2007 |
| WO | 2007117399 A2 | 10/2007 |
| WO | 2007120339 A1 | 10/2007 |
| WO | 2008000922 A1 | 1/2008 |
| WO | 2008038011 A1 | 4/2008 |
| WO | 2008040951 A1 | 4/2008 |
| WO | 2008071587 A2 | 6/2008 |
| WO | 2008079719 A1 | 7/2008 |
| WO | 2008092199 A1 | 8/2008 |
| WO | WO 2009/115583 | * 9/2009 |
| WO | 2009158571 A1 | 12/2009 |

OTHER PUBLICATIONS

Simone, Oncology: Introduction, Cecil Textbook of Medicine, 20th Edition, vol. 1, pp. 1004-1101 O, 1996.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Pearce et al., Failure modes in anticancer drug discovery and development, Cancer Drug Design and Discovery Edited by Stephen Neidle, Chapter 18, pp. 424-435 (2008).*
Linz et al., CAPLUS Abstract 151:381395 (2009).*

(Continued)

*Primary Examiner* — Deepak Rao
(74) *Attorney, Agent, or Firm* — Michael P. Morris; Alan R. Stempel

(57) ABSTRACT

The present invention includes compounds of general formula (1)

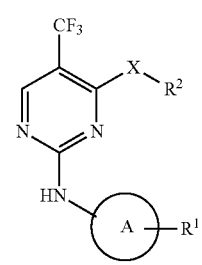

(1)

wherein
A, X, $R^1$ and $R^2$ are defined as in claim 1, which are suitable for the treatment of diseases characterized by excessive or abnormal cell proliferation, and their use for preparing a medicament having the above-mentioned properties.

3 Claims, No Drawings

(56) References Cited

OTHER PUBLICATIONS

International Search Report, Form PCT/ISA/210, for corresponding PCT/EP2009/065762; date of mailing: Mar. 4, 2010.
Verma et al.; Substituted aminobenzimidazole pyrimidines as cyclin-dependent kinase inhibitors; Bioorganic & Medicinal Chemistry Letters; 2005; No. 15; pp. 1973-1977.
Ahmed FASEB Journal 18; 2004; pp. 5-7.
Snyder et al.; J. Med. Liban.; 2000; vol. 48(4); pp. 208-214.
Sugar et al.; Diagn. Microbiol. Infect. Dis.; 1995; vol. 21; pp. 129-133.
Turner et al.; Current Pharmaceutical Design; 1996; vol. 2; pp. 209-224.
Cohen et al., Current Opinion in Chemical Biology, 1999, vol. 3, pp. 459-465.
Freshney et al., Culture of Animal Cells, A Manual of Basic Technique, Alan R. Liss, Inc., 1983, p. 4.
Dermer et al., BIO/Technology, 1994, 12:320.
Powell et al., British Journal of Dermatology, 1999, 141, pp. 802-810.
Golub et al., Science, 1999, 286, pp. 531-537.
Mass et al., Int. J. Radiation Oncology Bio. Phys. vol. 2004, 58(3), pp. 932-940.
Fabbro et al., Pharmacology & Therapeutics, 2002, 93, pp. 79-98.
Pinedo et al, Translational Research: The role of VEGF in Tumor Angiogenesis, Department of Medical Oncology, 2000, vol. 5 (suppl 1), pp. 1-2.
McMahon et al., VEGF Receptor Signaling in Tumor Angiogenesis, The Oncologist, 2000, vol. 5 (suppl 1), pp. 3-10.

* cited by examiner

PYRIMIDINE DERIVATIVES THAT INHIBIT FAK/PTK2

The present invention relates to new pyrimidines of general formula (1)

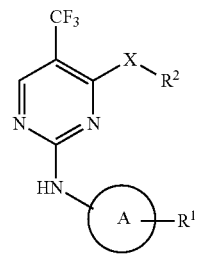

(1)

wherein the groups A, X, $R^1$ and $R^2$ have the meanings given in the claims and specification, the isomers thereof, processes for preparing these pyrimidines and their use as medicaments.

BACKGROUND TO THE INVENTION

Tumour cells that acquire the properties for invasion and metastasisation require specific survival signals. These signals allow them to overcome special apoptosis mechanisms (anoikis) which are triggered, inter alia, by the loss of cell adhesion. In this process, focal adhesion kinase (FAK/PTK2) is one of the essential signal molecules which on the one hand controls cell-matrix interactions through so-called 'focal adhesions' and on the other hand imparts anoikis resistance. Interference with these mechanisms by inhibiting PTK2 may lead to the apoptotic cell death of tumour cells and limit the invasive and metastasising growth of tumours. In addition, focal adhesion kinase has major significance for the growth, migration and survival of tumour-associated endothelial cells. An anti-angiogenic activity may therefore also be achieved by inhibiting PTK2.

Pyrimidines are generally known as inhibitors of kinases. Thus, for example, in International Patent Application WO 2008038011, pyrimidines are described as Aurora Kinase inhibitors, these pyrimidines having an oxymethylpiperidine group in the 4-position and fluorine in the 5-position as substituents.

The aim of the present invention is to indicate new active substances which can be used for the prevention and/or treatment of diseases characterised by excessive or abnormal cell proliferation.

DETAILED DESCRIPTION OF THE INVENTION

It has been found that, surprisingly, compounds of general formula (1), wherein the groups A, X, $R^1$ and $R^2$ have the meanings given below, act as inhibitors of specific tyrosine-kinases. Thus, the compounds according to the invention may be used for example for treating diseases connected with the activity of specific tyrosine-kinases and characterised by excessive or abnormal cell proliferation.

The present invention relates to compounds of general formula (1)

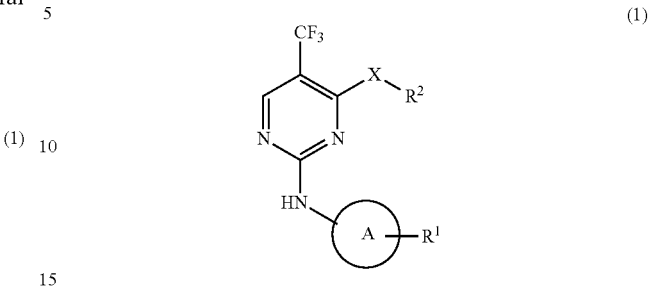

(1)

wherein
A denotes a group, optionally substituted by one or more, identical or different $R^1$, selected from among $C_{6-15}$aryl and 5-12 membered heteroaryl;
X denotes O, S or $CH_2$;
$R^1$ denotes hydrogen or a group selected from among $R^a$, $R^b$ and $R^a$ substituted by one or more, identical or different $R^c$ and/or $R^b$
$R^2$ denotes a group selected from among $R^a$ and $R^a$ substituted by one or more, identical or different $R^b$ and/or $R^c$;
each $R^a$ is selected independently of one another from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;
each $R^b$ is a suitable group and each is independently selected from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^c)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C(NR^g)NR^cR^c$,
each $R^c$ independently of one another denotes hydrogen or a group optionally substituted by one or more, identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;
each $R^d$ is a suitable group and each is independently selected from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^e$ $R^e$, —$NR^eR^e$, —$ONR^eR^e$, —$N(R^g)NR^eR^e$, halogen, —$CF_3$, —CN, —NC, —OCN, —SCN, —NO, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$ —$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$, each $R^e$ independently of one another denotes hydrogen or a group optionally substituted by one or more, identical or different $R^f$ and/or $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl;

each $R^f$ is a suitable group and each is independently selected from among halogen and —$CF_3$; and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl or 6-18 membered heteroarylalkyl;

optionally in the form of the tautomers, the racemates, the enantiomers, the diastereomers and the mixtures thereof, and optionally the pharmacologically acceptable acid addition salts thereof.

In one aspect the invention relates to compounds of general formula (1), wherein A is a group selected from among phenyl and 5-10 membered heteroaryl.

In another aspect the invention relates to compounds of general formula (1), wherein A is phenyl.

In another aspect the invention relates to compounds of general formula (1), wherein X denotes O.

In another aspect the invention relates to compounds of general formula (1), wherein $R^2$ is a group selected from among $C_{1-6}$alkyl, $C_{3-8}$cycloalkyl, $C_{6-10}$aryl, 3-8 membered heterocycloalkyl and 5-12 membered heteroaryl, optionally substituted by one or more, identical or different $R^b$ and/or $R^c$.

In another aspect the invention relates to compounds of general formula (1), wherein $R^2$ is a group selected from among $C_{6-10}$aryl and 5-12 membered heteroaryl, optionally substituted by one or more, identical or different $R^b$ and/or $R^c$.

In another aspect the invention relates to compounds of general formula (1) selected from the group consisting of

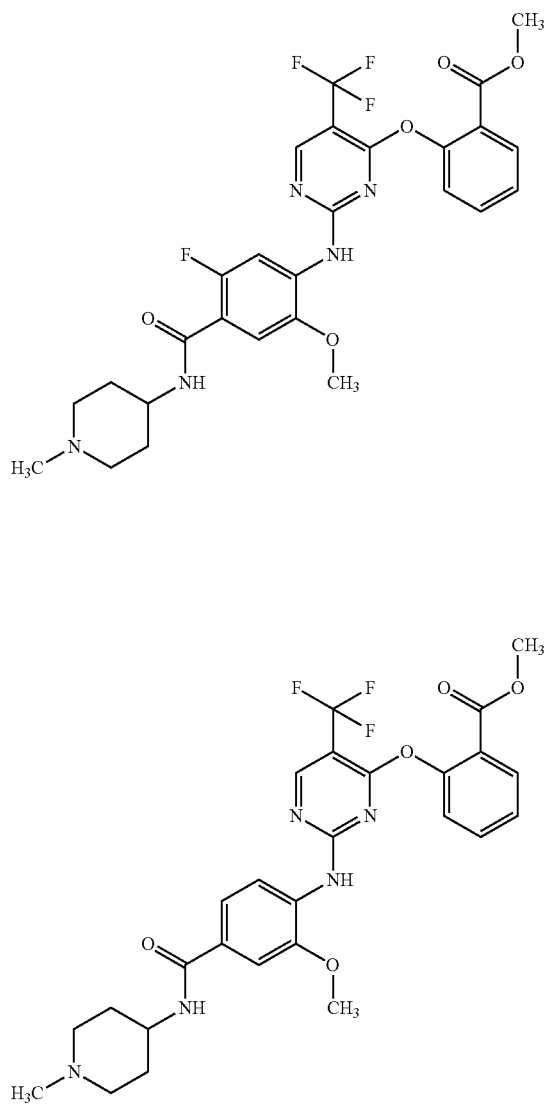

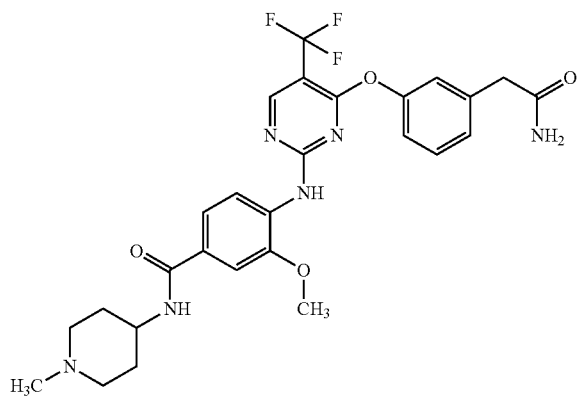

5
-continued
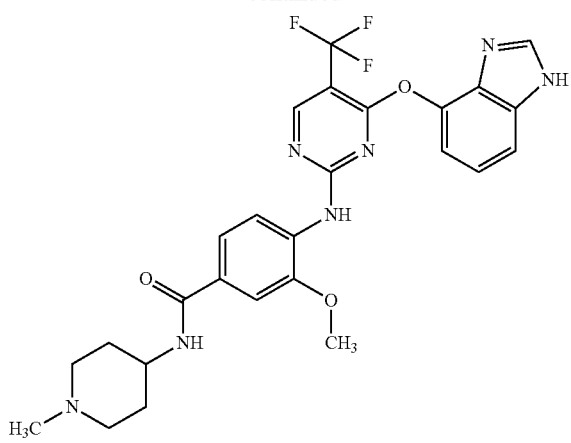
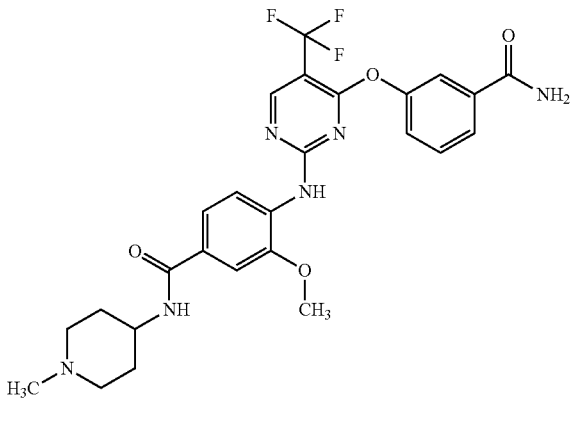
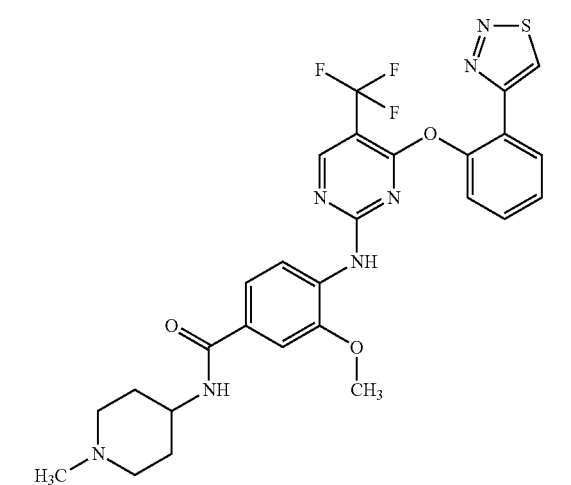
6
-continued
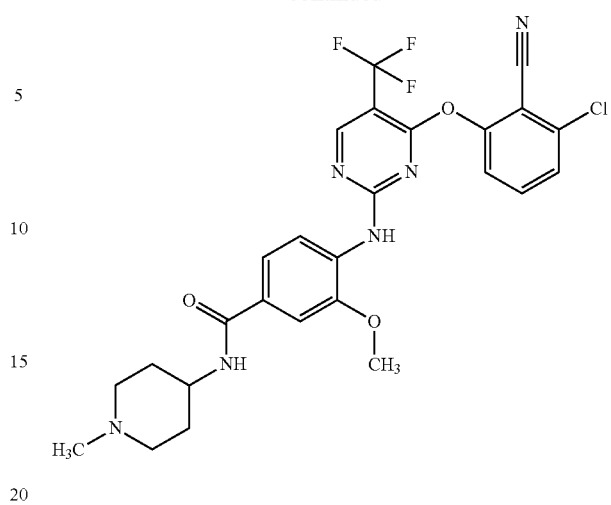

7
-continued
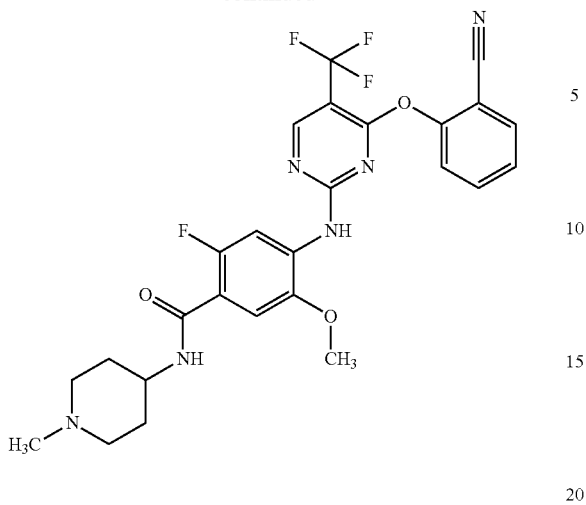
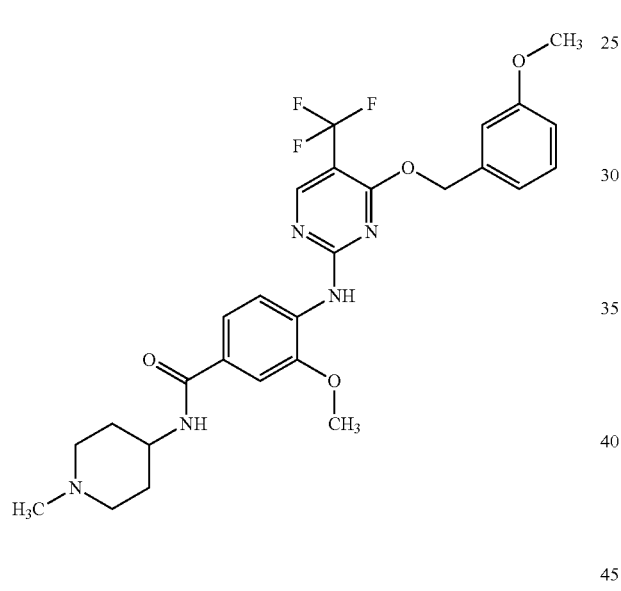
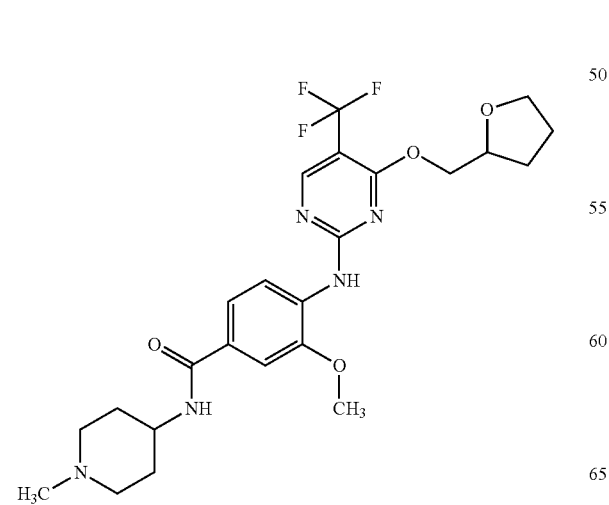
8
-continued
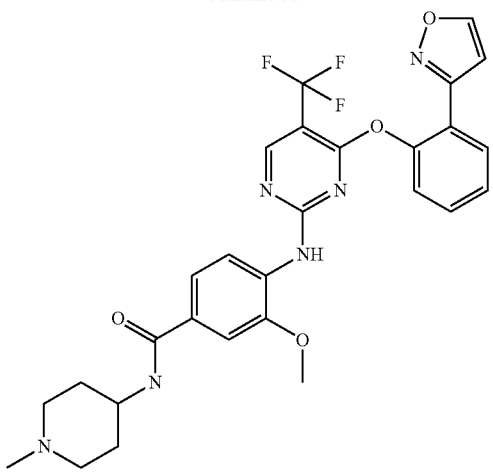
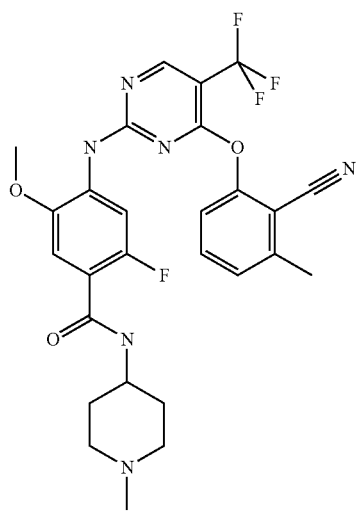
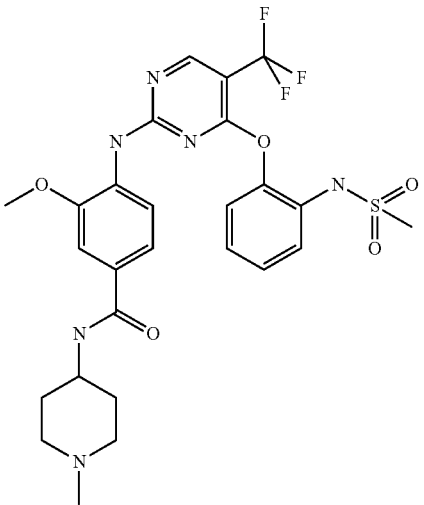

9
-continued
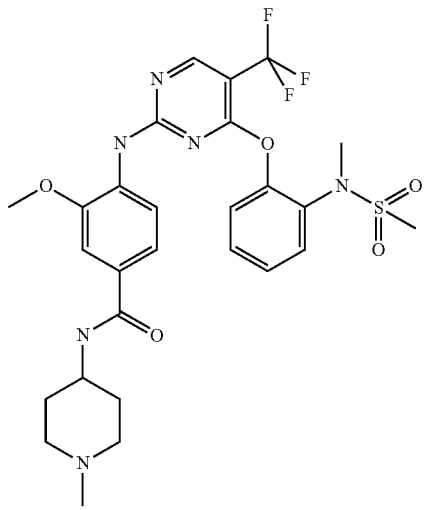
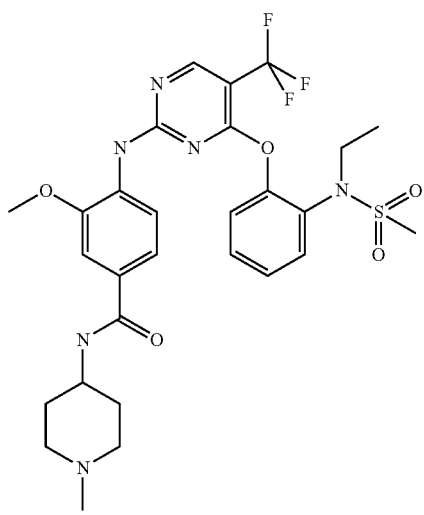
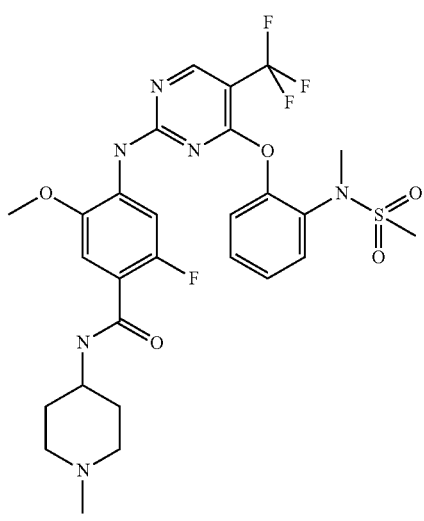
10
-continued
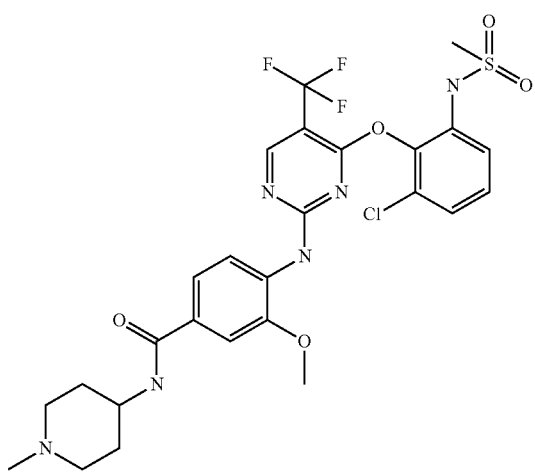
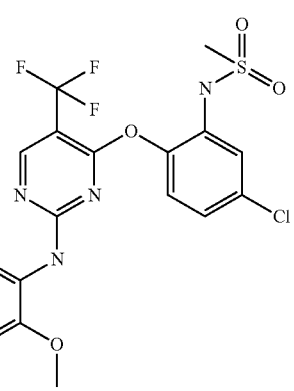
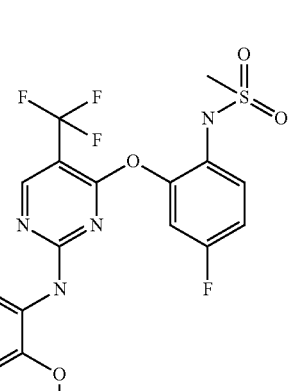

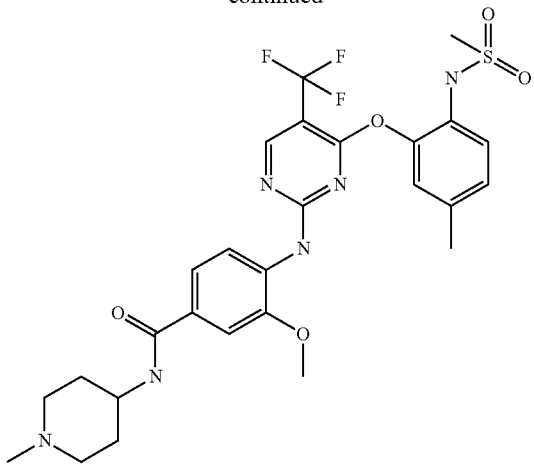

In another aspect the invention relates to compounds, or the pharmaceutically effective salts thereof, of general formula (1) for use as medicaments.

In another aspect the invention relates to compounds, or the pharmaceutically effective salts thereof, of general formula (1) for preparing a medicament with an antiproliferative and/or pro-apoptotic activity.

In another aspect the invention relates to pharmaceutical preparations, containing as active substance one or more compounds of general formula (1) or the physiologically acceptable salts thereof optionally in combination with conventional excipients and/or carriers.

In another aspect the invention relates to the use of compounds of general formula (1) for preparing a pharmaceutical composition for the treatment and/or prevention of cancer, infections, inflammatory or autoimmune diseases.

In another aspect the invention relates to pharmaceutical preparations comprising a compound of general formula (1) and at least one further cytostatic or cytotoxic active substance, different from formula (1), optionally in the form of the tautomers, the racemates, the enantiomers, the diastereomers and the mixtures thereof, and optionally the pharmacologically acceptable acid addition salts thereof.

DEFINITIONS

As used herein, the following definitions apply, unless stated otherwise:

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl contains at least one triple bond. If a hydrocarbon chain were to carry both at least one double bond and also at least one triple bond, by definition it would belong to the alkynyl sub-group. All the sub-groups mentioned above may further be divided into straight-chain (unbranched) and branched. If an alkyl is substituted, the substitution may be mono- or polysubstitution in each case, at all the hydrogen-carrying carbon atoms, independently of one another.

Examples of representatives of individual sub-groups are listed below.

Straight-Chain (Unbranched) or Branched Saturated Hydrocarbon Chains:

methyl; ethyl; n-propyl; isopropyl(1-methylethyl); n-butyl; 1-methylpropyl; isobutyl(2-methylpropyl); sec.-butyl(1-methylpropyl); tert.-butyl(1,1-dimethylethyl); n-pentyl; 1-methylbutyl; 1-ethylpropyl; isopentyl(3-methylbutyl); neopentyl(2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chain (Unbranched) or Branched Alkenyl:

vinyl(ethenyl); prop-1-enyl; allyl(prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. without any further definition are meant saturated hydrocarbon groups with the corresponding number of carbon atoms, all the isomeric forms being included.

By the terms propenyl, butenyl, pentenyl, hexenyl, heptenyl, octenyl, nonenyl, decenyl etc. without any further definition are meant unsaturated hydrocarbon groups with the corresponding number of carbon atoms and a double bond, all the isomeric forms, i.e. (Z)/(E) isomers, being included where applicable.

By the terms butadienyl, pentadienyl, hexadienyl, heptadienyl, octadienyl, nonadienyl, decadienyl etc. without any further definition are meant unsaturated hydrocarbon groups with the corresponding number of carbon atoms and two double bonds, all the isomeric forms, i.e. (Z)/(E) isomers, being included where applicable.

By the terms propynyl, butynyl, pentynyl, hexynyl, heptynyl, octynyl, nonynyl, decynyl etc. without any further definition are meant unsaturated hydrocarbon groups with the corresponding number of carbon atoms and a triple bond, all the isomeric forms being included.

By the term heteroalkyl are meant groups which can be derived from the alkyl as defined above in its broadest sense if, in the hydrocarbon chains, one or more of the groups —CH$_3$ are replaced independently of one another by the groups —OH, —SH or —NH$_2$, one or more of the groups —CH$_2$— are replaced independently of one another by the groups —O—, —S— or —NH—, one or more of the groups

are replaced by the group

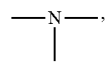

one or more of the groups =CH— are replaced by the group =N—, one or more of the groups =CH$_2$ are replaced by the group =NH or one or more of the groups =CH are replaced by the group =N, while overall there may only be a maximum of three heteroatoms in a heteroalkyl, there must be at least one carbon atom between two oxygen atoms and between two sulphur atoms or between one oxygen and one sulphur atom and the group as a whole must be chemically stable.

It is immediately apparent from the indirect definition/derivation from alkyl that heteroalkyl is made up of the sub-groups saturated hydrocarbon chains with heteroatom(s), heteroalkenyl and heteroalkynyl, and one further subdivision may be carried out into straight-chain (unbranched) and branched. If a heteroalkyl is substituted, the substitution may be mono- or polysubstitution in each case, at all the hydrogen-carrying oxygen, sulphur, nitrogen and/or carbon atoms, independently of one another. Heteroalkyl itself may be linked to the molecule as a substituent both via a carbon atom and via a heteroatom.

Typical examples are listed below:
dimethylaminomethyl; dimethylaminoethyl(1-dimethylaminoethyl; 2-dimethylaminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl(1-diethylaminopropyl, 2-diethylaminopropyl, 3-diethylaminopropyl); diisopropylaminoethyl(1-diisopropylaminoethyl, 2-diisopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Halogen denotes fluorine, chlorine, bromine and/or iodine atoms.

Haloalkyl is derived from alkyl as hereinbefore defined in its broadest sense, when one or more hydrogen atoms of the hydrocarbon chain are replaced independently of one another by halogen atoms, which may be identical or different. It is immediately apparent from the indirect definition/derivation from alkyl that haloalkyl is made up of the sub-groups saturated halohydrocarbon chains, haloalkenyl and haloalkynyl, and further subdivision may be made into straight-chain (unbranched) and branched. If a haloalkyl is substituted, the substitution may be mono- or polysubstitution in each case, at all the hydrogen-carrying carbon atoms, independently of one another.

Typical examples include —$CF_3$; —$CHF_2$; —$CH_2F$; —$CF_2CF_3$; —$CHFCF_3$; —$CH_2CF_3$; —$CF_2CH_3$; —$CHFCH_3$; —$CF_2CF_2CF_3$; —$CF_2CH_2CH_3$; —CF=$CF_2$; —CCl=$CH_2$; —CBr=$CH_2$; —CI=$CH_2$; —C≡C—$CF_3$; —$CHFCH_2CH_3$; and —$CHFCH_2CF_3$.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). The term unsaturated means that in the ring system in question there is at least one double bond, but no aromatic system is formed. In bicyclic hydrocarbon rings two rings are linked such that they have at least two carbon atoms in common. In spirohydrocarbon rings one carbon atom (spiroatom) is shared by two rings. If a cycloalkyl is substituted, the substitution may be mono- or polysubstitution in each case, at all the hydrogen-carrying carbon atoms, independently of one another. Cycloalkyl itself may be linked to the molecule as substituent via any suitable position of the ring system.

Typical examples of individual sub-groups are listed below.

Monocyclic Saturated Hydrocarbon Rings:
cyclopropyl; cyclobutyl; cyclopentyl; cyclohexyl; cycloheptyl etc.

Monocyclic Unsaturated Hydrocarbon Rings:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.

Saturated and Unsaturated Bicyclic Hydrocarbon Rings:
bicyclo[2.2.0]hexyl; bicyclo[3.2.0]heptyl; bicyclo[3.2.1]octyl; bicyclo[2.2.2]octyl; bicyclo[4.3.0]nonyl(octahydroindenyl); bicyclo[4.4.0]decyl(decahydronaphthalene); bicyclo[2,2,1]heptyl(norbornyl); (bicyclo[2.2.1]hepta-2,5-dienyl (norborna-2,5-dienyl); bicyclo[2,2,1]hept-2-enyl (norbornenyl); bicyclo[4.1.0]heptyl(norcaranyl); bicyclo-[3.1.1]heptyl(pinanyl) etc.

Saturated and Unsaturated Spirohydrocarbon Rings:
spiro[2.5]octyl, spiro[3.3]heptyl, spiro[4.5]dec-2-ene etc.

Cycloalkylalkyl denotes the combination of the above-defined groups alkyl and cycloalkyl, in each case in their broadest sense. The alkyl group as substituent is directly linked to the molecule and is in turn substituted by a cycloalkyl group. The alkyl and cycloalkyl may be linked in both groups via any carbon atoms suitable for this purpose. The respective sub-groups of alkyl and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system. Typical examples include phenyl, naphthyl, indanyl(2,3-dihydroindenyl), 1,2,3,4-tetrahydronaphthyl and fluorenyl.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples include benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.

Monocyclic Heteroaryls:
furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls:

indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydrothienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-S-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —$CH_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —$SO_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-5-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydropyrimidinyl; dihydrofuryl; dihydropyranyl; tetrahydrothienyl-5-oxide; tetrahydrothienyl-S,S-dioxide; homothiomorpholinyl-5-oxide; 2,3-dihydroazet; 2H-pyrrolyl; 4H-pyranyl; 1,4-dihydropyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl; hexahydro-furo[3,2-b]furyl; etc.

Spiro-Heterorings (Saturated and Unsaturated):

1,4-dioxa-spiro[4.5]decyl; 1-oxa-3,8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

By the term "suitable substituent" is meant a substituent that on the one hand is fitting on account of its valency and on the other hand leads to a system with chemical stability.

By "prodrug" is meant an active substance in the form of its precursor metabolite. A distinction may be made between partly multi-part carrier-prodrug systems and biotransformation systems. The latter contain the active substance in a form that requires chemical or biological metabolisation. The skilled man will be familiar with prodrug systems of this kind (Sloan, Kenneth B.; Wasdo, Scott C. The role of prodrugs in penetration enhancement. Percutaneous Penetration Enhancers (2nd Edition) (2006). 51-64; Lloyd, Andrew W. Prodrugs. Smith and Williams' Introduction to the Principles of Drug Design and Action (4th Edition) (2006), 211-232; Neervannan, Seshadri. Strategies to impact solubility and dissolution rate during drug lead optimization: salt selection and prodrug design approaches. American Pharmaceutical Review (2004), 7(5), 108.110-113). A suitable prodrug contains for example a substance of the general formulae which is linked via an enzymatically cleavable linker (e.g. carbamate, phosphate, N-glycoside or a disulphide group to a dissolution-improving substance (e.g. tetraethyleneglycol, saccharides, amino acids). Carrier-prodrug systems contain the active substance as such, bound to a masking group which can be cleaved by the simplest possible controllable mechanism. The function of masking groups according to the invention in the compounds according to the invention is to neutralise the charge for improving cell uptake. If the compounds according to the invention are used with a masking group, these may also additionally influence other pharmacological parameters, such as for example oral bioavailability, tissue distribution, pharmacokinetics and stability against non-specific phosphatases. The delayed release of the active substance may also involve a sustained-release effect. In addition, modified metabolisation may occur, thus resulting in a higher efficiency of the active substance or organic specificity. In the case of a prodrug formulation, the masking group or a linker that binds the masking group to the active substance is selected such that the prodrug is sufficiently hydrophilic to be dissolved in the blood serum, has sufficient chemical and enzymatic stability to reach the activity site and is also sufficiently hydrophilic to ensure that it is suitable for diffusion-controlled membrane transport. Furthermore, it should allow chemically or enzymatically induced release of the active substance within a reasonable period and, it goes without saying, the auxiliary components released should be non-toxic. Within the scope of the invention, however, the compound without a mask or linker, and a mask, may be regarded as a prodrug which first of all has to be prepared in the cell from the ingested compound by enzymatic and biochemical processes.

LIST OF ABBREVIATIONS abs. absolute, anhydrous
Ac acetyl
Bn benzyl
Boc tert.-butyloxycarbonyl
Bu butyl
c concentration
chex cyclohexane
d day(s)
TLC thin layer chromatography
DCM dichloromethane
DEA diethylamine
DIPEA N-ethyl-N,N-diisopropylamine (Hünig base)
DMF N,N-dimethylformamide
DMSO dimethylsulphoxide
EE ethyl acetate (ethyl acetate)
eq equivalent(s)
ESI electron spray ionization
Et ethyl
EtOH ethanol
h hour
HATU O-(7-azabenzotriazol-1-yl)-N,N,N',N'-tetramethyl-uronium tetrafluorophosphate
hex hexyl
HPLC high performance liquid chromatography
i iso
IR infrared spectroscopy
cat. catalyst, catalytic
conc. concentrated
b.p. boiling point
LC liquid chromatography
soln. solution
Me methyl
MeOH methanol
min minutes
MPLC medium pressure liquid chromatography
MS mass spectrometry
NMP N-methylpyrrolidone
NP normal phase
Ph phenyl
Pr propyl
Py pyridine
rac racemic
$R_f$ (Rf) retention factor
RP reversed phase
RT ambient temperature
TBTU O-(benzotriazol-1-yl)-N,N,N',N'-tetramethyl-uronium tetrafluoroborate
temp. temperature
tert. tertiary
TFA trifluoroacetic acid
THF tetrahydrofuran
$t_{Ret.}$ retention time (HPLC)
UV ultraviolet

| List of abbreviations | |
|---|---|
| abs. | absolute, anhydrous |
| Ac | acetyl |
| Bn | benzyl |
| Boc | tert.-butyloxycarbonyl |
| Bu | butyl |
| c | concentration |
| chex | cyclohexane |
| d | day(s) |
| TLC | thin layer chromatography |
| DCM | dichloromethane |
| DEA | diethylamine |
| DIPEA | N-ethyl-N,N-diisopropylamine (Hünig base) |
| DMF | N,N-dimethylformamide |
| DMSO | dimethylsulphoxide |
| EE | ethyl acetate (ethyl acetate) |
| eq | equivalent(s) |
| ESI | electron spray ionization |
| Et | ethyl |
| EtOH | ethanol |
| h | hour |
| HATU | O-(7-azabenzotriazol-1-yl)-N,N,N',N'-tetramethyl-uronium tetrafluorophosphate |
| hex | hexyl |
| HPLC | high performance liquid chromatography |
| i | iso |
| IR | infrared spectroscopy |
| cat. | catalyst, catalytic |
| conc. | concentrated |
| b.p. | boiling point |
| LC | liquid chromatography |
| soln. | solution |
| Me | methyl |
| MeOH | methanol |
| min | minutes |
| MPLC | medium pressure liquid chromatography |
| MS | mass spectrometry |
| NMP | N-methylpyrrolidone |
| NP | normal phase |
| Ph | phenyl |
| Pr | propyl |
| Py | pyridine |
| rac | racemic |
| $R_f$ (Rf) | retention factor |
| RP | reversed phase |
| RT | ambient temperature |
| TBTU | O-(benzotriazol-1-yl)-N,N,N',N'-tetramethyl-uronium tetrafluoroborate |
| temp. | temperature |
| tert. | tertiary |
| TFA | trifluoroacetic acid |
| THF | tetrahydrofuran |
| $t_{Ret.}$ | retention time (HPLC) |
| UV | ultraviolet |

Features and advantages of the present invention will become apparent from the following detailed Examples which illustrate the fundamentals of the invention by way of example, without restricting its scope:
Preparation of the Compounds According to the Invention
General All the reactions are carried out—unless stated otherwise—in commercially obtainable apparatus using methods conventionally used in chemical laboratories.

Air- and/or moisture-sensitive starting materials are stored under protective gas and corresponding reactions and manipulations using them are carried out under protective gas (nitrogen or argon).

Microwave reactions are carried out in an Initiator made by Biotage or an Explorer made by CEM in sealed containers (preferably 2, 5 or 20 mL), preferably with stirring.

Chromatography

For the preparative medium pressure chromatography (MPLC, normal phase) silica gel is used which is made by Millipore (named: Granula Silica Si-60A 35-70 µm) or C-18 RP-silica gel (RP-phase) made by Macherey Nagel (named: Polygoprep 100-50 C18).

The thin layer chromatography is carried out on ready-made silica gel 60 TLC plates on glass (with fluorescence indicator F-254) made by Merck.

The preparative high pressure chromatography (HPLC) is carried out using columns made by Waters (named: XTerra Prep. MS C18, 5 µM, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18 5 µm OBD 19×50 mm), Agilent (named: Zorbax SB-C8 5 µm PrepHT 21.2×50 mm) and Phenomenex (named: Gemini C18 5 µm AXIA 21.2×50 mm or Gemini C18 10 µm 50×150 mm), the analytical HPLC (reaction control) is carried out with columns made by Agilent (named: Zorbax SB-C8, 5 µm, 21.2×50 mm or Zorbax SB-C8 3.5 µm 2.1×50 mm) and Phenomenex (named: Gemini C18 3 µm 2×30 mm).

HPLC Mass Spectroscopy/UV Spectrometry

The retention times/MS-ESI$^+$ for characterising the examples are obtained using an HPLC-MS apparatus (high performance liquid chromatography with mass detector) made by Agilent. Compounds that elute with the injection peak are given the retention time $t_{Ret.}$=0.00.

Method A:
  Column: Waters, Xterra MS C18, 2.5 µm, 2.1×30 mm, Part. No. 186000592
  Eluant: A: $H_2O$ with 0.1% HCOOH; B: acetonitrile (HPLC grade)
  Detection: MS: Positive and negative mode
  Mass range: 120-900 m/z
  Fragmentor: 120
  Gain EMV: 1; Threshold: 150; Stepsize: 0.25; UV: 254 nm; Bandwidth: 1
  Injection: Inj. Vol. 5 µL
  Separation: Flow 1.10 mL/min
  Column temp.: 40° C.
  Gradient:
    0.00 min: 5% solvent B
    0.00-2.50 min: 5%→95% solvent B
    2.50-2.80 min: 95% solvent B
    2.81-3.10 min: 95%→5% solvent B
Method B:
  Column: Waters, Xterra MS C18, 2.5 µm, 2.1×50 mm, Part. No. 186000594
  Eluant: A: $H_2O$ with 0.1% HCOOH; B: acetonitrile with 0.1% HCOOH
  Detection: MS: Positive and negative mode
  Mass range: 100-1200 m/z
  Fragmentor: 70
  Gain EMV: Threshold: 1 mAU; Stepsize: 2 nm; UV: 254 nm as well as 230 nm
  Injection: Standard 1 µL
  Flow: 0.6 mL/min
  Column temp.: 35° C.
  Gradient:
    0.00 min: 5% solvent B
    0.00-2.50 min: 5%→95% solvent B
    2.50-4.00 min: 95% solvent B
    4.00-4.50 min: 95%→5% solvent B
    4.50-6.00 min: 95% solvent A
Method C:
  Column: Waters, X-Bridge C18, 3.5 µm, 2.1×50 mm,
  Eluant: A: $H_2O$ with 10 mM $NH_3$; B: acetonitrile with 10 nM $NH_3$
  Detection: MS: Positive and negative mode
  Mass range: 100-800 m/z
  Fragmentor: 70
  Gain EMV: Threshold: 1 mAU; Stepsize: 2 nm; UV: 220-320 nm
  Injection: Standard 1 µL
  Flow: 0.8 mL/min
  Column temp.: 25° C.
  Gradient:
    0.00 min: 2% solvent B
    0.00-4.00 min: 2%→98% solvent B
    4.00-6.00 min: 98% solvent B
Method D:
  Column: Waters, X-Bridge C18, 3.5 µm, 2.1×50 mm,
  Eluant: A: $H_2O$ with 0.1% HCOOH; B: acetonitrile with 0.1% HCOOH
  Detection: MS: Positive and negative mode
  Mass range: 100-800 m/z
  Fragmentor: 70
  Gain EMV: Threshold: 1 mAU; Stepsize: 2 nm; UV: 220-320 nm
  Injection: Standard 1 µL
  Flow: 0.8 mL/min
  Column temp.: 35° C.
  Gradient:
    0.00 min: 2% solvent B
    0.00-4.00 min: 2%→98% solvent B
    4.00-6.00 min: 98% solvent B
Method E:
  Column: Phenomenex Gemini C18, 3.0 µm, 2.0×50 mm,
  Eluant: A: $H_2O$ with 10 mM $NH_3$; B: acetonitrile with 10 nM $NH_3$
  Detection: MS: Positive and negative mode
  Mass range: 100-800 m/z
  Fragmentor: 70
  Gain EMV: Threshold: 1 mAU; Stepsize: 2 nm; UV: 220-320 nm
  Injection: Standard 1 µL
  Flow: 1.0 mL/min
  Column temp.: 35° C.
  Gradient:
    0.00 min: 2% solvent B
    0.00-3.50 min: 2%→98% solvent B
    3.50-6.00 min: 98% solvent B
Method F:
  Column: Phenomenex Gemini C18, 3.0 m, 2.0×50 mm,
  Eluant: A: $H_2O$ with 0.1% HCOOH; B: acetonitrile with 0.1% HCOOH
  Detection: MS: Positive and negative mode
  Mass range: 100-800 m/z
  Fragmentor: 70
  Gain EMV: Threshold: 1 mAU; Stepsize: 2 nm; UV: 220-320 nm
  Injection: Standard 1 µL
  Flow: 1.0 mL/min
  Column temp.: 35° C.

Gradient:
    0.00 min: 2% solvent B
    0.00-3.50 min: 2%→98% solvent B
    3.50-6.00 min: 95% solvent B Method A:

| Column: | Waters, Xterra MS C18, 2.5 µm, 2.1 × 30 mm, Part. No. 186000592 |
|---|---|
| Eluant: | A: H$_2$O with 0.1% HCOOH; B: acetonitrile (HPLC grade) |
| Detection: | MS: Positive and negative mode |
| Mass range: | 120-900 m/z |
| Fragmentor: | 120 |
| Gain EMV: | 1; Threshold: 150; Stepsize: 0.25; UV: 254 nm; Bandwidth: 1 |
| Injection: | Inj. Vol. 5 µL |
| Separation: | Flow 1.10 mL/min |
| Column temp.: | 40° C. |
| Gradient: | 0.00 min: 5% solvent B<br>0.00-2.50 min: 5% → 95% solvent B<br>2.50-2.80 min: 95% solvent B<br>2.81-3.10 min: 95% → 5% solvent B |

Method B:

| Column: | Waters, Xterra MS C18, 2.5 µm, 2.1 × 50 mm, Part. No. 186000594 |
|---|---|
| Eluant: | A: H$_2$O with 0.1% HCOOH; B: acetonitrile with 0.1% HCOOH |
| Detection: | MS: Positive and negative mode |
| Mass range: | 100-200 m/z |
| Fragmentor: | 70 |
| Gain EMV: | Threshold: 1 mAU; Stepsize: 2 nm; UV: 254 nm as well as 230 nm |
| Injection: | Standard 1 µL |
| Flow: | 0.6 mL/min |
| Column temp.: | 35° C. |
| Gradient: | 0.00 min: 5% solvent B<br>0.00-2.50 min: 5% → 95% solvent B<br>2.50-4.00 min: 95% solvent B<br>4.00-4.50 min: 95% → 5% solvent B<br>4.50-6.00 min: 95% solvent A |

Method C:

| Column: | Waters, X-Bridge C18, 3.5 µm, 2.1 × 50 mm, |
|---|---|
| Eluant: | A: H$_2$O with 10 mM NH$_3$; B: acetonitrile with 10 nM NH$_3$ |
| Detection: | MS: Positive and negative mode |
| Mass range: | 100-800 m/z |
| Fragmentor: | 70 |
| Gain EMV: | Threshold: 1 mAU; Stepsize: 2 nm; UV: 220-320 nm |
| Injection: | Standard 1 µL |
| Flow: | 0.8 mL/min |
| Column temp.: | 25° C. |
| Gradient: | 0.00 min: 2% solvent B<br>0.00-4.00 min: 2% → 98% solvent B<br>4.00-6.00 min: 98% solvent B |

Method D:

| Column: | Waters, X-Bridge C18, 3.5 µm, 2.1 × 50 mm, |
|---|---|
| Eluant: | A: H$_2$O with 0.1% HCOOH; B: acetonitrile with 0.1% HCOOH |
| Detection: | MS: Positive and negative mode |
| Mass range: | 100-800 m/z |
| Fragmentor: | 70 |
| Gain EMV: | Threshold: 1 mAU; Stepsize: 2 nm; UV: 220-320 nm |
| Injection: | Standard 1 µL |
| Flow: | 0.8 mL/min |
| Column temp.: | 35° C. |
| Gradient: | 0.00 min: 2% solvent B<br>0.00-4.00 min: 2% → 98% solvent B<br>4.00-6.00 min: 98% solvent B |

Method E:

| Column: | Phenomenex Gemini C18, 3.0 µm, 2.0 × 50 mm, |
|---|---|
| Eluant: | A: H$_2$O with 10 mM NH$_3$; B: acetonitrile with 10 nM NH$_3$ |
| Detection: | MS: Positive and negative mode |
| Mass range: | 100-800 m/z |
| Fragmentor: | 70 |
| Gain EMV: | Threshold: 1 mAU; Stepsize: 2 nm; UV: 220-320 nm |
| Injection: | Standard 1 µL |
| Flow: | 1.0 mL/min |
| Column temp.: | 35° C. |
| Gradient: | 0.00 min: 2% solvent B<br>0.00-3.50 min: 2% → 98% solvent B<br>3.50-6.00 min: 98% solvent B |

Method F:

| Column: | Phenomenex Gemini C18, 3.0 µm, 2.0 × 50 mm, |
|---|---|
| Eluant: | A: H$_2$O with 0.1% HCOOH; B: acetonitrile with 0.1% HCOOH |
| Detection: | MS: Positive and negative mode |
| Mass range: | 100-800 m/z |
| Fragmentor: | 70 |
| Gain EMV: | Threshold: 1 mAU; Stepsize: 2 nm; UV: 220-320 nm |
| Injection: | Standard 1 µL |
| Flow: | 1.0 mL/min |
| Column temp.: | 35° C. |
| Gradient: | 0.00 min: 2% solvent B<br>0.00-3.50 min: 2% → 98% solvent B<br>3.50-6.00 min: 95% solvent B |

The compounds according to the invention are prepared by the methods of synthesis described below, in which the substituents of the general formulae have the meanings specified hereinbefore. These methods are intended to illustrate the invention without restricting it to their content or limiting the scope of the compounds claimed to these Examples. Where the preparation of the starting compounds is not described, they are commercially obtainable or may be prepared analogously to known compounds or methods described herein. Substances described in the literature are prepared according to the published methods of synthesis.

Reaction scheme A

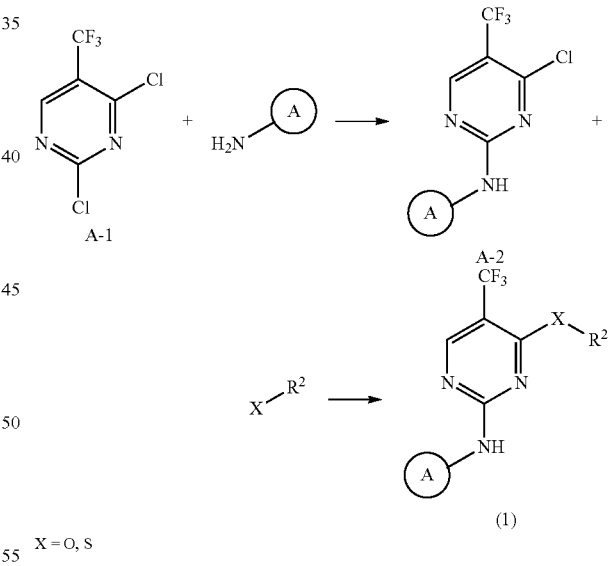

X = O, S

Example compounds of type (1) are prepared from 2,4-dichloro-5-trifluoromethylpyrimidine A-1 by nucleophilic aromatic substitution of the chlorine in position 2 of the pyrimidine using an amine A-NH$_2$ and subsequent exchange of the second chlorine with an alcohol OR$^2$ or a sulphide SR$^2$ or by coupling benzyl metal halides HalMetR$^2$. A and R$^2$ are both suitable groups for arriving at the example compounds.

The nucleophilic aromatic substitutions at A-1 and A-2 are carried out using methods known from the literature in common solvents, such as for example THF, DCM, NMP, toluene, DMSO or DMF using a base, such as for example DIPEA, LiOH, $Cs_2CO_3$, or KOtBu, an acid such as HCl or a Lewis acid such as $ZnCl_2$. The amines $A-NH_2$, the alcohols $OR^2$, the sulphides $SR^2$ and the organometallic compounds used are commercially obtainable or may be synthesised using methods known from the literature. The 2-amino-4-oxo-5-trifluoromethylpyrimidines or the thio- or carbo-analogous compounds of type (1) which may be obtained directly by these reaction methods may be further modified in A and $R^2$ at a suitable point in a manner known from the literature or in a manner analogous thereto to form other derivatives of type (1). Thus, for example, the groups A and $R^2$ of directly accessible 2-amino-4-oxo-5-trifluoromethylpyrimidines or 2-amino-4-thio-5-trifluoromethylpyrimidines of type (1), which consist of a carboxylic acid, sulphonic acid, halo- or amino-substituted aryl or heteroaryl, may be converted by reactions of substitution (at the heteroaryl itself), alkylation, acylation, amination or addition.

Starting Materials

The starting materials, if the preparation thereof is not described, are commercially obtainable, known from the literature or readily obtainable by the skilled man using general methods, for example 4-amino-2-fluoro-5-methoxy-benzoic acid (WO 2008040951), 4-(4-chloro-5-trifluoromethyl-pyrimidin-2-ylamino)-benzoic acid (WO 2007003596)

4-(4-chloro-5-trifluoromethyl-pyrimidin-2-ylamino)-3-methoxy-benzoic acid, 4-(4-chloro-5-trifluoromethyl-pyrimidin-2-ylamino)-2-fluoro-5-methoxy-benzoic acid, (analogously to WO 2007003596)

Example 1

3-methoxy-N-(1-methyl-piperidin-4-yl)-4-(4-phenoxy-5-trifluoromethyl-pyrimidin-2-ylamino)-benzamide a) Synthesis of 4-(4-chloro-5-trifluoromethyl-pyrimidin-2-ylamino)-3-methoxy-N-(1-methyl-piperidin-4-yl)-benzamide

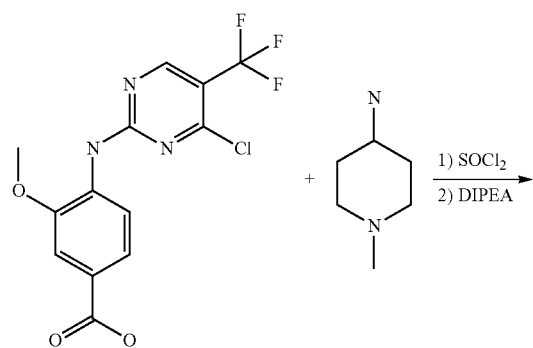

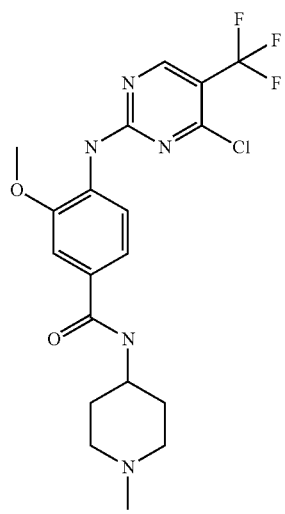

4-(4-chloro-5-trifluoromethyl-pyrimidin-2-ylamino)-3-methoxy-benzoic acid (5 g) is suspended in toluene (150 mL) and combined with thionyl chloride (1.77 mL), stirred for 2 h at 110° C. and after cooling the solvent is eliminated in vacuo. The residue is taken up in THF (50 mL), cooled to 0° C. and a solution of 4-amino-1-methylpiperidine (1.396 g) and diisopropylethylamine (4.19 mL) is added dropwise thereto. Then the reaction mixture is left to warm up to RT and stirred overnight. After filtering, the residue is dried overnight at 50° C.

b) Synthesis of 3-methoxy-N-(1-methyl-piperidin-4-yl)-4-(4-phenoxy-5-trifluoromethyl-pyrimidin-2-ylamino)-benzamide

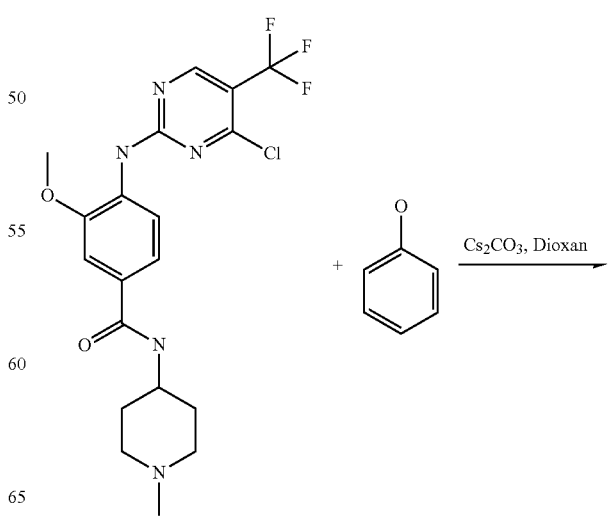

-continued

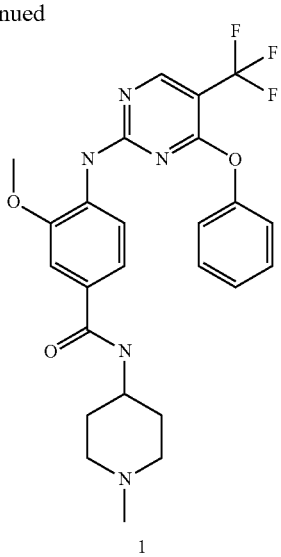

1

4-(4-chloro-5-trifluoromethyl-pyrimidin-2-ylamino)-3-methoxy-N-(1-methyl-piperidin-4-yl)-benzamide (50 mg) and phenol (21.3 mg) are dissolved in dioxane (0.3 mL). Pyridine (36.4 µL) and $Cs_2CO_3$ (235 mg) are added and the suspension is stirred overnight at 80° C. Then the reaction mixture is diluted with methanol (5 mL) and mixed with isolute. The solvent is eliminated in vacuo and then the mixture is purified by preparative HPLC. (PTK2 $IC_{50}$=35 nmol)

The following compounds 2 to 51 are synthesised analogously, with the corresponding 4-chloro-5-trifluoromethylpyrimidines as educts:

Examples 2-51

| No. | Structure | $t_{Ret}$ (HPLC) [min] | MS (M + H)$^+$ | PTK2 $IC_{50}$ [nM] |
|---|---|---|---|---|
| 2 | 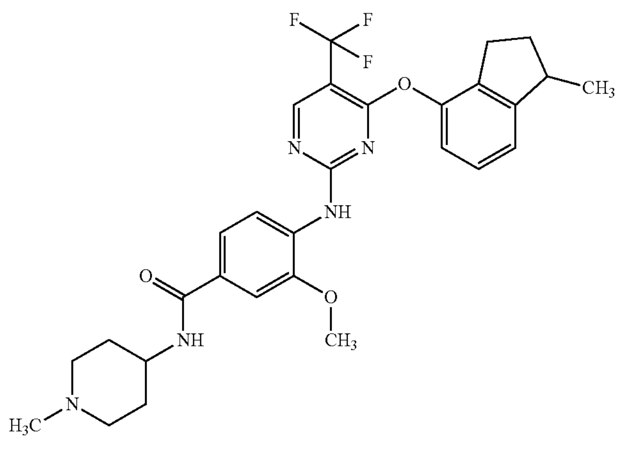 | 2.35 | 556 | 88 |
| 3 | 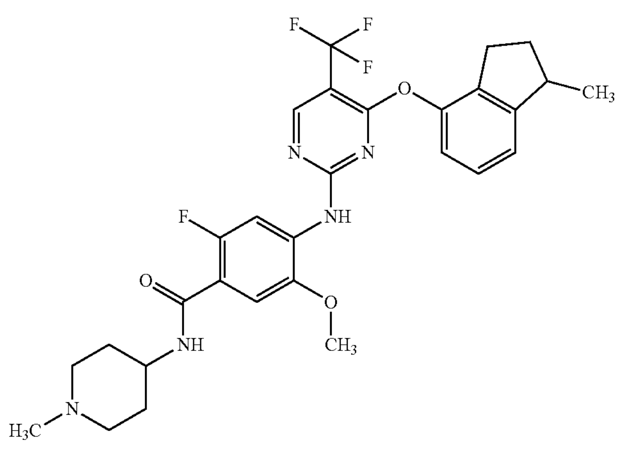 | 2.43 | 574 | 99 |

-continued

| No. | Structure | t_Ret (HPLC) [min] | MS (M + H)+ | PTK2 IC50 [nM] |
|---|---|---|---|---|
| 4 | 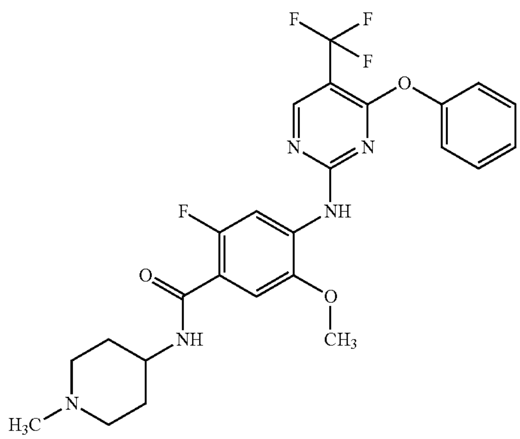 [SMILES: COc1cc(C(=O)NC2CCN(C)CC2)c(F)cc1Nc1ncc(C(F)(F)F)c(Oc2ccccc2)n1] | 2.03 | 520 | 48 |
| 5 | 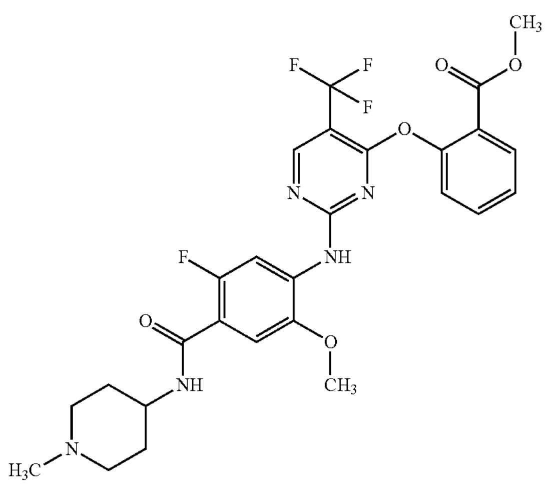 | 1.89 | 462 | 11 |
| 6 | 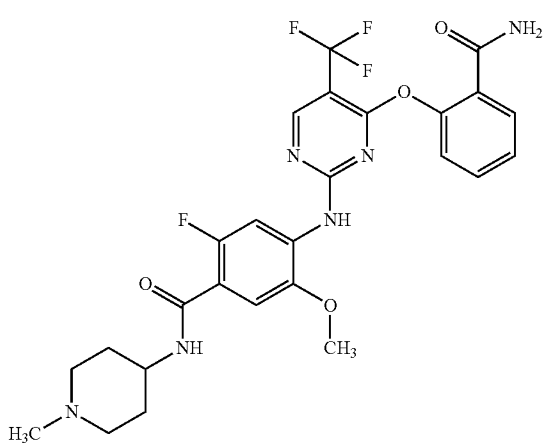 [SMILES: COc1cc(C(=O)NC2CCN(C)CC2)c(F)cc1Nc1ncc(C(F)(F)F)c(Oc2ccccc2C(N)=O)n1] | 1.20 | 563 | 52 |

-continued

| No. | Structure | $t_{Ret}$(HPLC) [min] | MS (M + H)⁺ | PTK2 IC$_{50}$ [nM] |
|---|---|---|---|---|
| 7 | 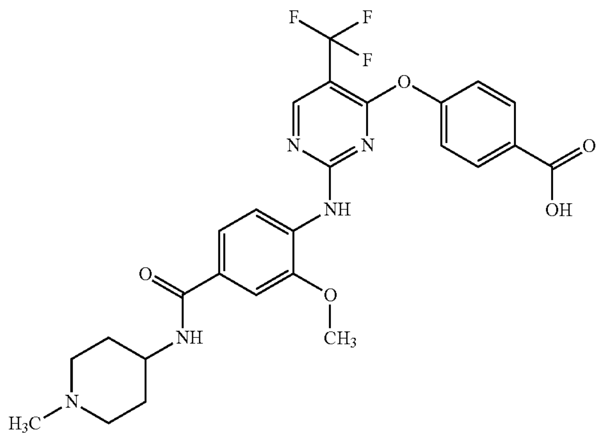 | 1.21 | 546 | 400 |
| 8 | 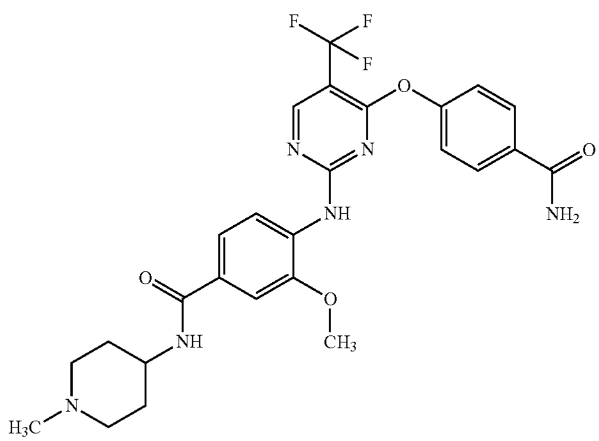 [SMILES: COc1cc(C(=O)NC2CCN(C)CC2)ccc1Nc1ncc(C(F)(F)F)c(Oc2ccc(C(=O)O)cc2)n1] | 1.65 | 545 | 30 |
| 9 | 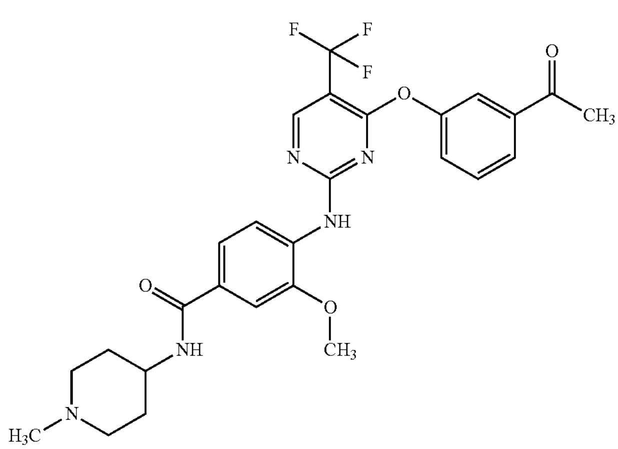 | 1.87 | 544 | 47 |

-continued

| No. | Structure | t_Ret (HPLC) [min] | MS (M + H)+ | PTK2 IC50 [nM] |
|---|---|---|---|---|
| 10 | 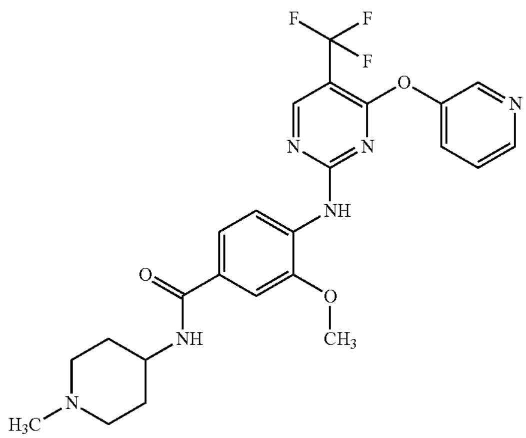 [SMILES: COc1cc(C(=O)NC2CCN(C)CC2)ccc1Nc1ncc(C(F)(F)F)c(Oc2cccnc2)n1] | 1.69 | 503 | 64 |
| 11 | 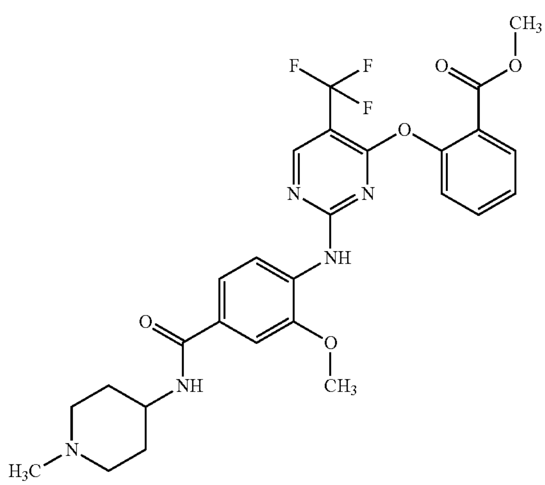 | 1.88 | 560 | 8 |
| 12 | 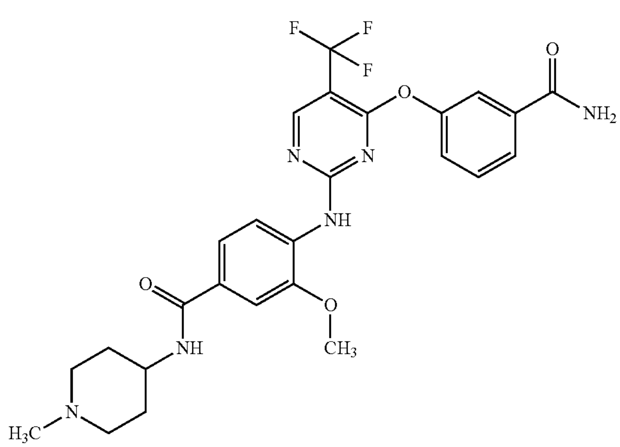 [SMILES: COc1cc(C(=O)NC2CCN(C)CC2)ccc1Nc1ncc(C(F)(F)F)c(Oc2cccc(C(N)=O)c2)n1] | 1.64 | 545 | 25 |

-continued

| No. | Structure | t<sub>Ret</sub>(HPLC) [min] | MS (M + H)+ | PTK2 IC$_{50}$ [nM] |
|---|---|---|---|---|
| 13 | 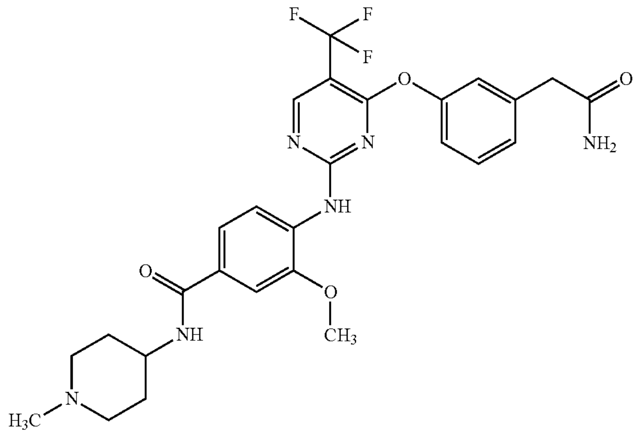 [SMILES: COc1cc(C(=O)NC2CCN(C)CC2)ccc1Nc1ncc(C(F)(F)F)c(Oc2cccc(CC(N)=O)c2)n1] | 1.61 | 559 | 17 |
| 14 | 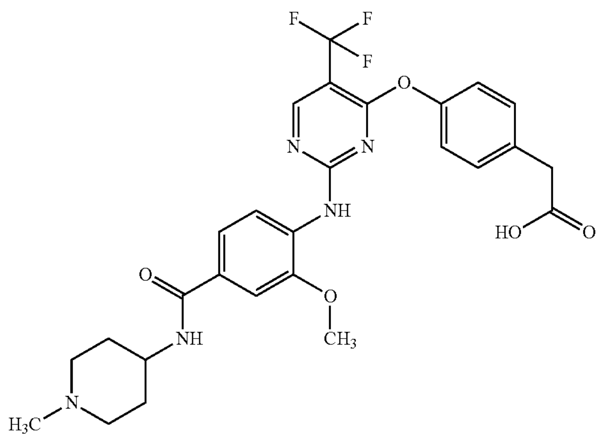 | 1.24 | 560 | 89 |
| 15 | 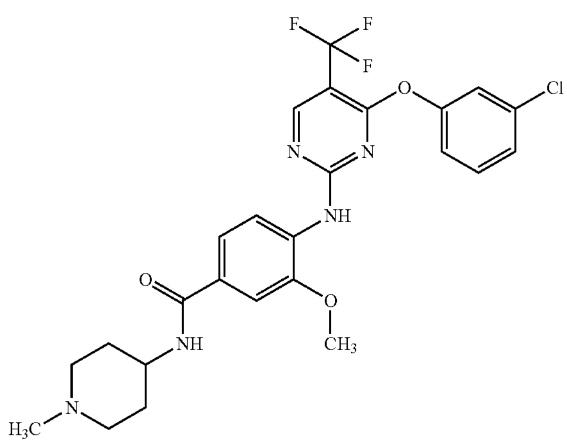 [SMILES: COc1cc(C(=O)NC2CCN(C)CC2)ccc1Nc1ncc(C(F)(F)F)c(Oc2cccc(Cl)c2)n1] | 2.04 | 536 | 64 |

-continued

| No. | Structure | t$_{Ret}$(HPLC) [min] | MS (M + H)$^+$ | PTK2 IC$_{50}$ [nM] |
|---|---|---|---|---|
| 16 | 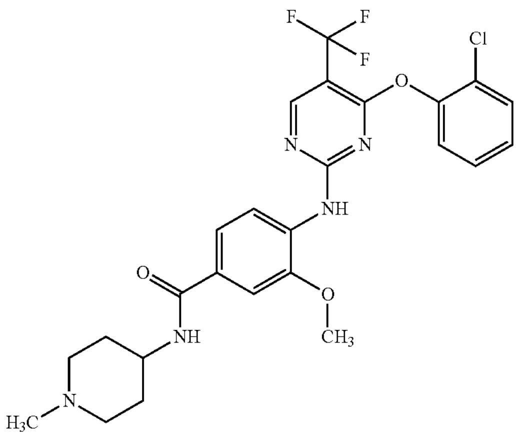 [SMILES: COc1cc(C(=O)NC2CCN(C)CC2)ccc1Nc1ncc(C(F)(F)F)c(Oc2ccccc2Cl)n1] | 1.98 | 536 | 85 |
| 17 | 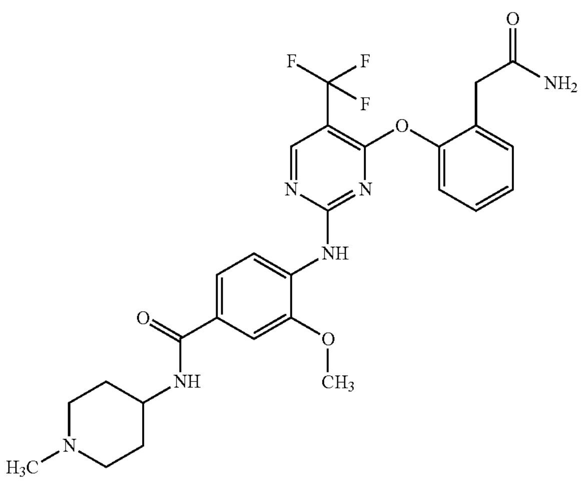 [SMILES: COc1cc(C(=O)NC2CCN(C)CC2)ccc1Nc1ncc(C(F)(F)F)c(Oc2ccccc2CC(N)=O)n1] | 1.63 | 559 | 78 |
| 18 | 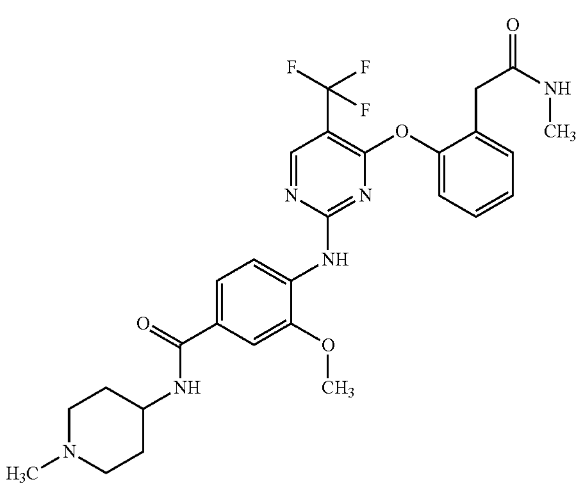 | 1.64 | 573 | 392 |

-continued

| No. | Structure | $t_{Ret}$ (HPLC) [min] | MS (M + H)$^+$ | PTK2 IC$_{50}$ [nM] |
|---|---|---|---|---|
| 19 | 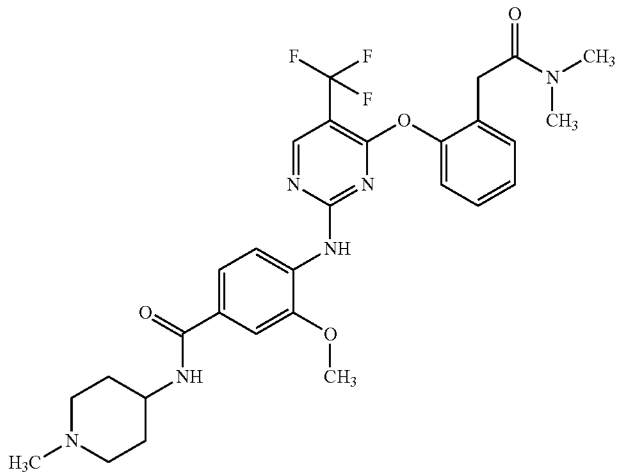 | 1.76 | 587 | 82 |
| 20 | 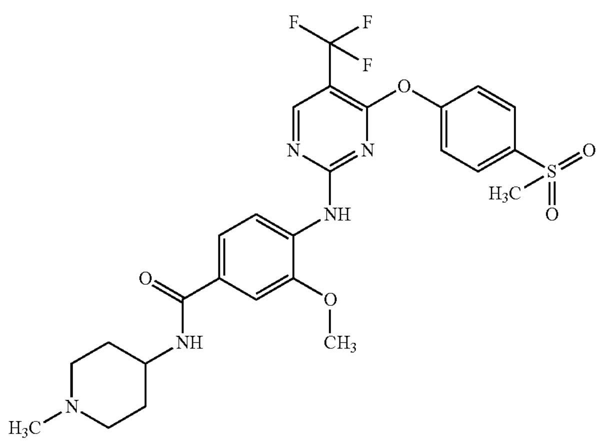 [SMILES: COc1cc(C(=O)NC2CCN(C)CC2)ccc1Nc1ncc(C(F)(F)F)c(Oc2ccc(S(C)(=O)=O)cc2)n1] | 1.76 | 580 | 114 |
| 21 | 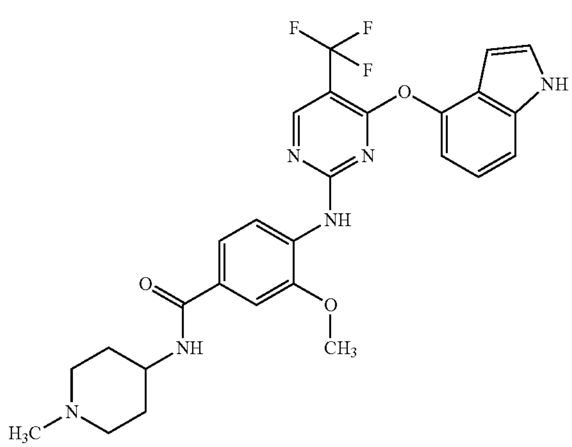 [SMILES: COc1cc(C(=O)NC2CCN(C)CC2)ccc1Nc1ncc(C(F)(F)F)c(Oc2cccc3[nH]ccc23)n1] | 1.87 | 541 | 43 |

| No. | Structure | t_Ret (HPLC) [min] | MS (M + H)+ | PTK2 IC50 [nM] |
|---|---|---|---|---|
| 22 | 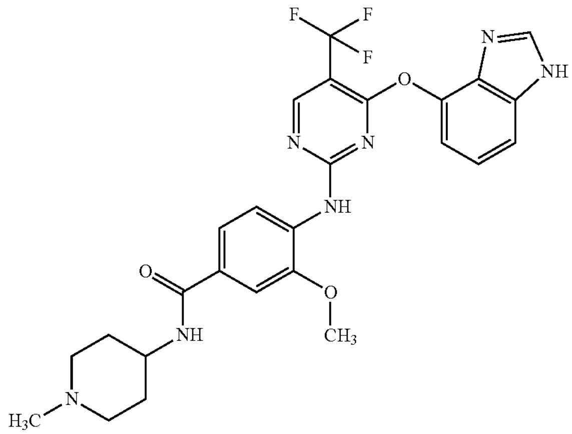 [SMILES: COc1cc(C(=O)NC2CCN(C)CC2)ccc1Nc1ncc(C(F)(F)F)c(Oc2cccc3[nH]cnc23)n1] | 1.66 | 542 | 19 |
| 23 | 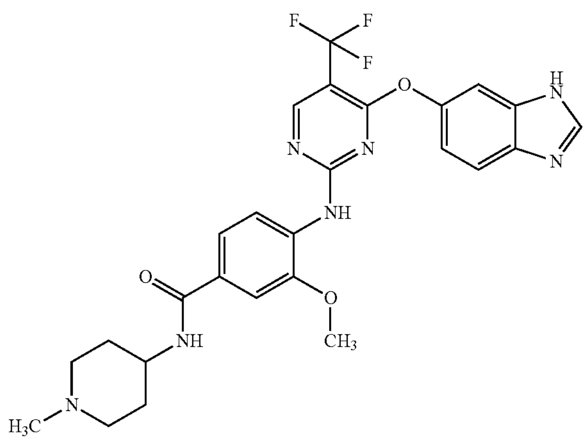 [SMILES: COc1cc(C(=O)NC2CCN(C)CC2)ccc1Nc1ncc(C(F)(F)F)c(Oc2ccc3nc[nH]c3c2)n1] | 1.65 | 542 | 38 |
| 24 | 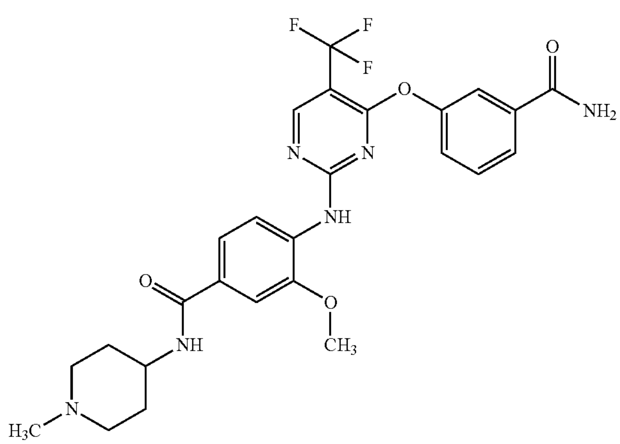 [SMILES: COc1cc(C(=O)NC2CCN(C)CC2)ccc1Nc1ncc(C(F)(F)F)c(Oc2cccc(C(N)=O)c2)n1] | 1.75 | 545 | 25 |

| No. | Structure | t_Ret (HPLC) [min] | MS (M + H)+ | PTK2 IC50 [nM] |
|---|---|---|---|---|
| 25 | (structure) | 1.79 | 559 | 74 |
| 26 | (structure) | 1.82 | 573 | 67 |
| 27 | (structure) | 1.73 | 559 | |

-continued

| No. | Structure | t_Ret (HPLC) [min] | MS (M + H)+ | PTK2 IC50 [nM] |
|---|---|---|---|---|
| 28 | 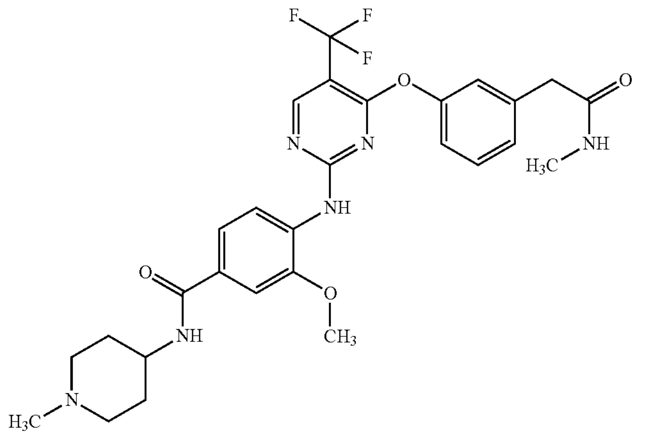 [SMILES: CNC(=O)Cc1cccc(Oc2nc(Nc3ccc(C(=O)NC4CCN(C)CC4)cc3OC)ncc2C(F)(F)F)c1] | 1.76 | 573 | 36 |
| 29 | 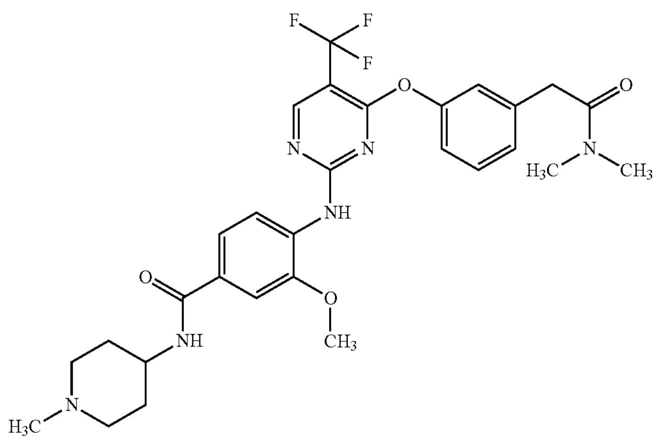 | 1.84 | 587 | 41 |
| 30 | 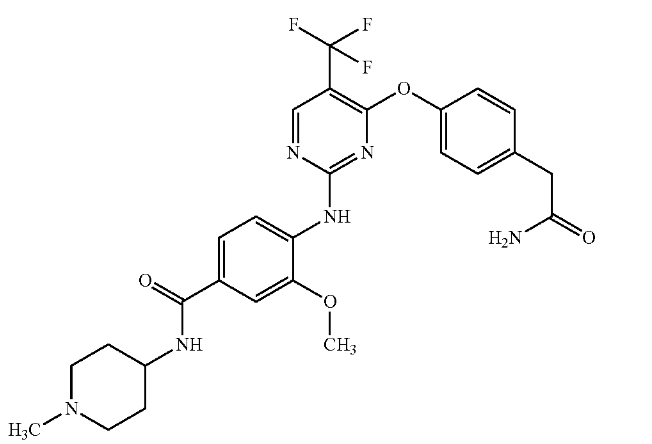 [SMILES: COc1cc(C(=O)NC2CCN(C)CC2)ccc1Nc1ncc(C(F)(F)F)c(Oc2ccc(CC(N)=O)cc2)n1] | 1.81 | 559 | 39 |

-continued

| No. | Structure | t_Ret (HPLC) [min] | MS (M + H)+ | PTK2 IC_50 [nM] |
|---|---|---|---|---|
| 31 | 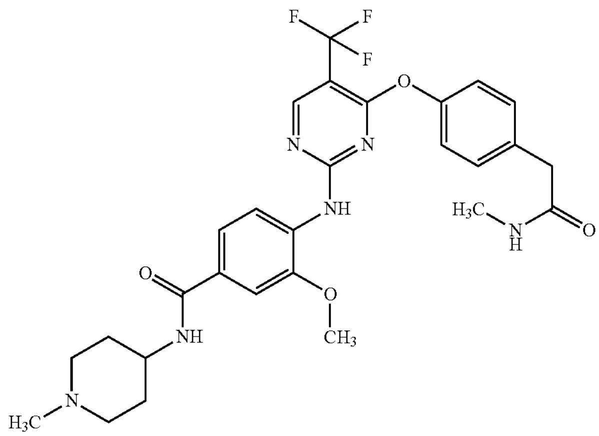 [SMILES: CNC(=O)Cc1ccc(Oc2nc(Nc3ccc(C(=O)NC4CCN(C)CC4)cc3OC)ncc2C(F)(F)F)cc1] | 1.78 | 573 | 49 |
| 32 | 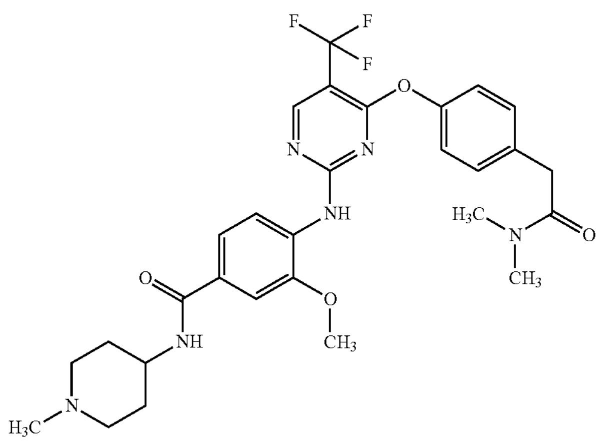 [SMILES: COc1cc(C(=O)NC2CCN(C)CC2)ccc1Nc1ncc(C(F)(F)F)c(Oc2ccc(CC(=O)N(C)C)cc2)n1] | 1.88 | 587 | 36 |
| 33 | 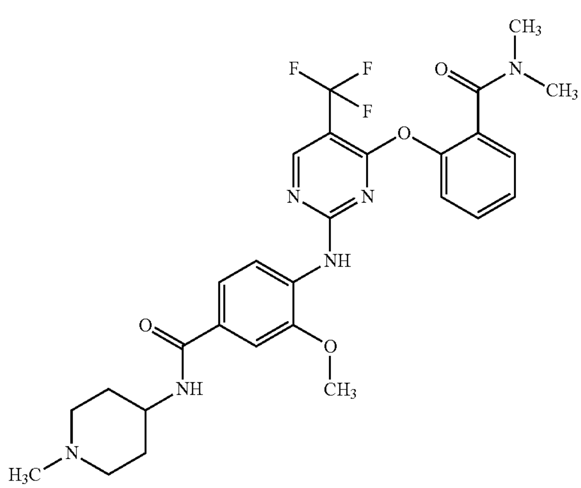 | 1.77 | 573 | 238 |

-continued
| No. | Structure | t_Ret (HPLC) [min] | MS (M + H)+ | PTK2 IC_{50} [nM] |
|---|---|---|---|---|
| 34 | 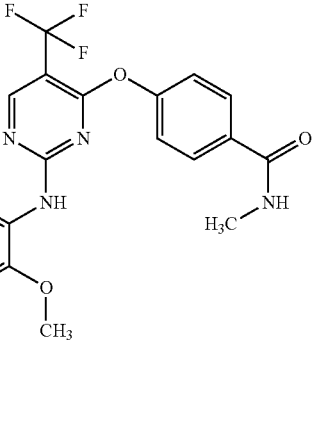 | 1.74 | 559 | 62 |
| 35 | 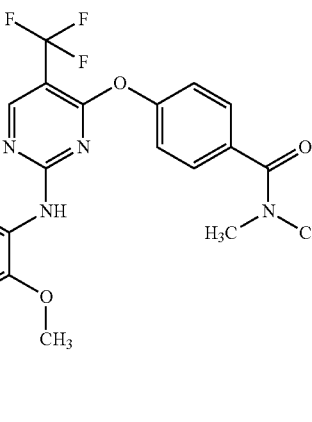 | 1.85 | 573 | 65 |
| 36 | 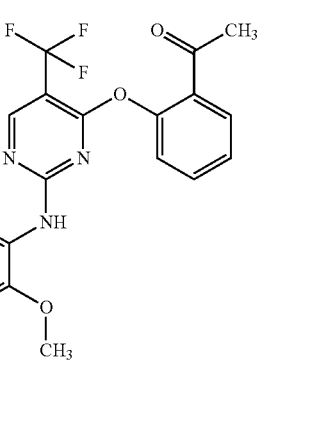 | 1.89 | 544 | 58 |

-continued

| No. | Structure | t_Ret (HPLC) [min] | MS (M + H)+ | PTK2 IC50 [nM] |
|---|---|---|---|---|
| 37 | 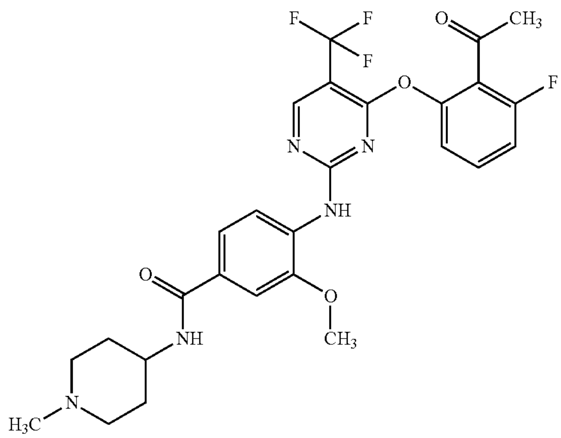 [SMILES: COc1cc(C(=O)NC2CCN(C)CC2)ccc1Nc1ncc(C(F)(F)F)c(Oc2cccc(F)c2C(C)=O)n1] | 1.75 | 562 | 139 |
| 38 | 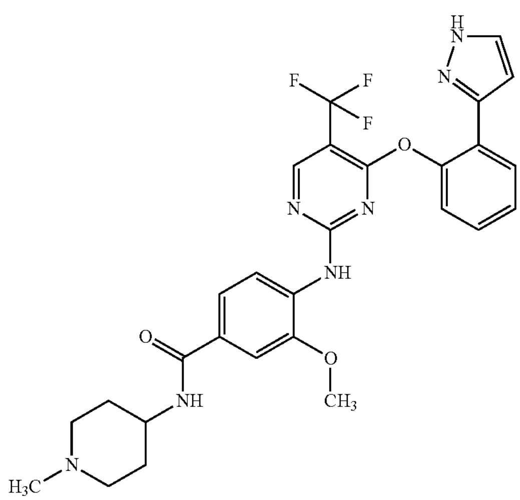 [SMILES: COc1cc(C(=O)NC2CCN(C)CC2)ccc1Nc1ncc(C(F)(F)F)c(Oc2ccccc2-c2cc[nH]n2)n1] | 2.17 | 568 | 81 |
| 39 | 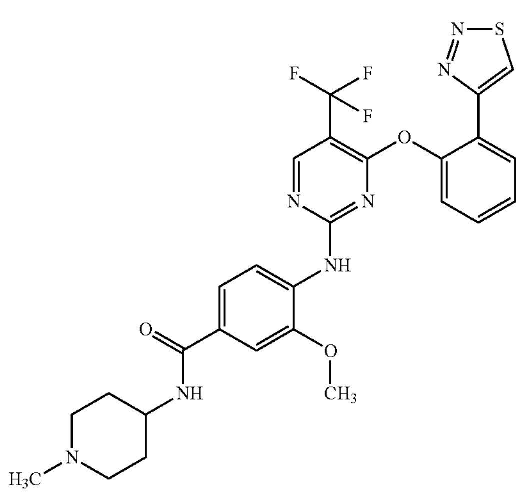 [SMILES: COc1cc(C(=O)NC2CCN(C)CC2)ccc1Nc1ncc(C(F)(F)F)c(Oc2ccccc2-c2csnn2)n1] | 2.07 | 586 | 12 |

-continued

| No. | Structure | t_Ret (HPLC) [min] | MS (M + H)+ | PTK2 IC_50 [nM] |
|---|---|---|---|---|
| 40 | 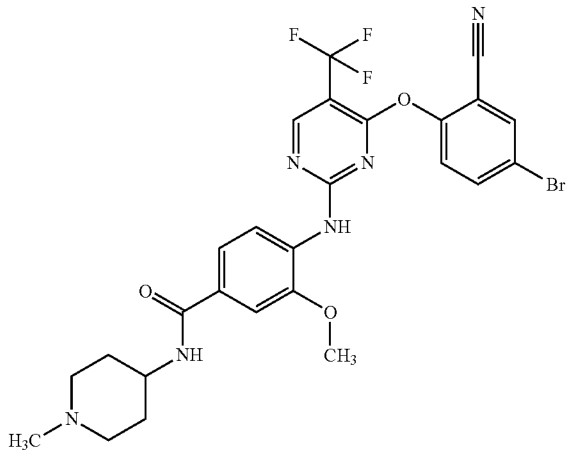 [SMILES: COc1cc(C(=O)NC2CCN(C)CC2)ccc1Nc1ncc(C(F)(F)F)c(Oc2ccc(Br)cc2C#N)n1] | 2.09 | 605 | 30 |
| 41 | 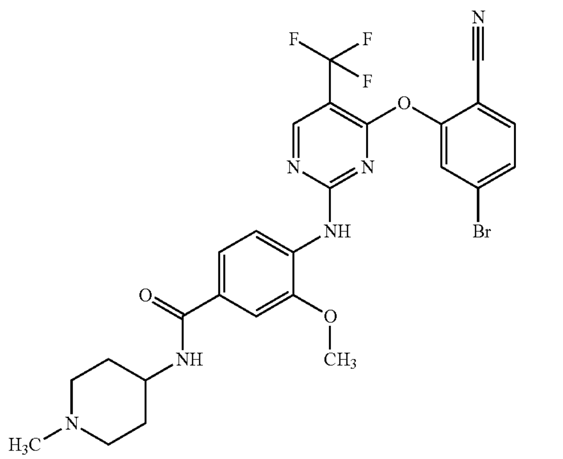 [SMILES: COc1cc(C(=O)NC2CCN(C)CC2)ccc1Nc1ncc(C(F)(F)F)c(Oc2cc(Br)ccc2C#N)n1] | 2.09 | 605 | 30 |
| 42 | 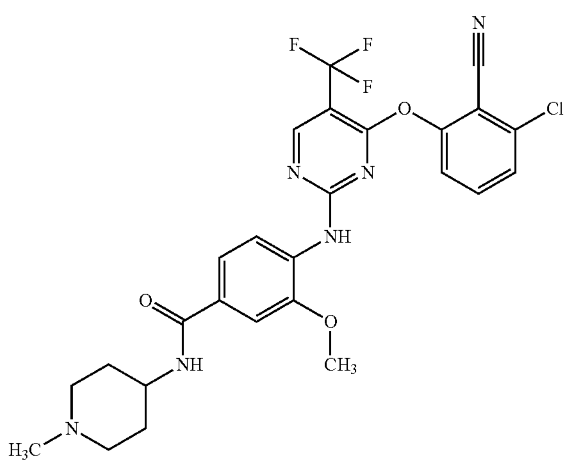 [SMILES: COc1cc(C(=O)NC2CCN(C)CC2)ccc1Nc1ncc(C(F)(F)F)c(Oc2cccc(Cl)c2C#N)n1] | 2.05 | 561 | 8 |

-continued

| No. | Structure | t_Ret (HPLC) [min] | MS (M + H)+ | PTK2 IC_50 [nM] |
|---|---|---|---|---|
| 43 | 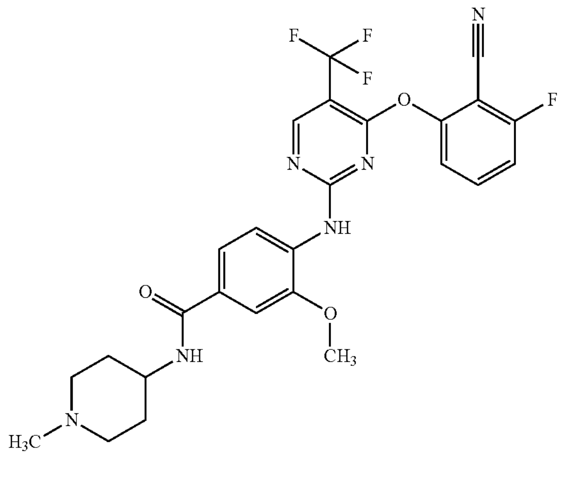 [SMILES: COc1cc(C(=O)NC2CCN(C)CC2)ccc1Nc1ncc(C(F)(F)F)c(Oc2cccc(F)c2C#N)n1] | 2.03 | 545 | 31 |
| 44 | 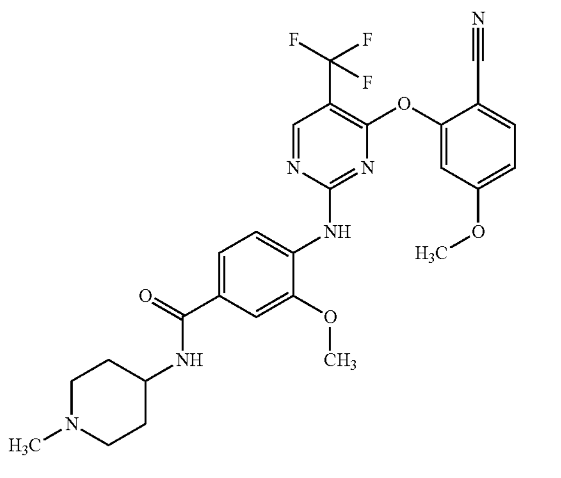 [SMILES: COc1ccc(C#N)c(Oc2nc(Nc3ccc(C(=O)NC4CCN(C)CC4)cc3OC)ncc2C(F)(F)F)c1] | 1.96 | 557 | 47 |
| 45 | 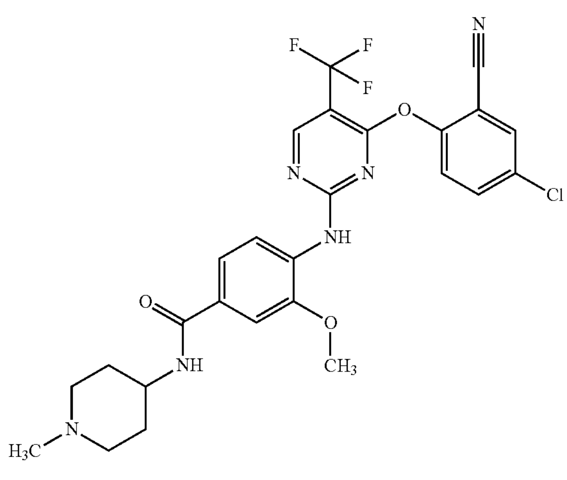 [SMILES: COc1cc(C(=O)NC2CCN(C)CC2)ccc1Nc1ncc(C(F)(F)F)c(Oc2ccc(Cl)cc2C#N)n1] | 2.04 | 561 | 20 |

-continued

| No. | Structure | t<sub>Ret</sub>(HPLC) [min] | MS (M + H)⁺ | PTK2 IC$_{50}$ [nM] |
|---|---|---|---|---|
| 46 | 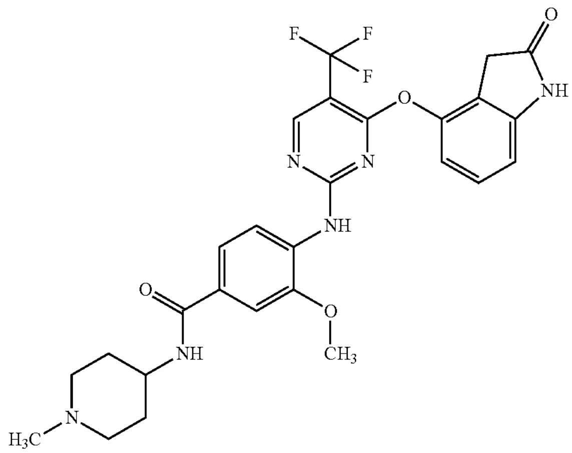 [SMILES: COc1cc(C(=O)NC2CCN(C)CC2)ccc1Nc1ncc(C(F)(F)F)c(Oc2cccc3c2CC(=O)N3)n1] | 1.88 | 557 | 69 |
| 47 | 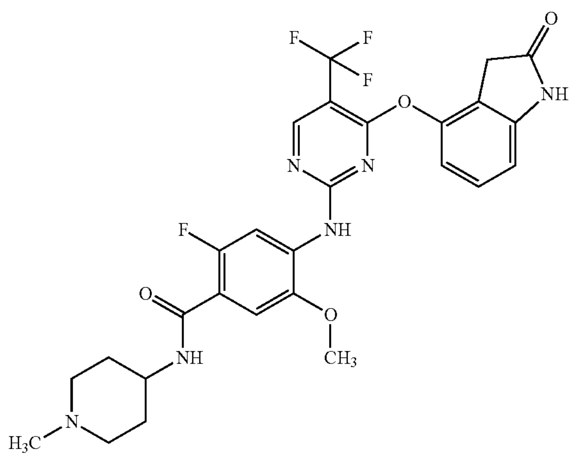 [SMILES: COc1cc(C(=O)NC2CCN(C)CC2)c(F)cc1Nc1ncc(C(F)(F)F)c(Oc2cccc3c2CC(=O)N3)n1] | 1.92 | 575 | 150 |
| 48 | 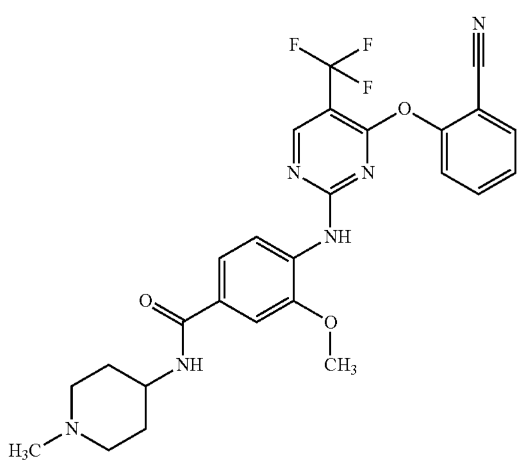 [SMILES: COc1cc(C(=O)NC2CCN(C)CC2)ccc1Nc1ncc(C(F)(F)F)c(Oc2ccccc2C#N)n1] | 2.03 | 527 | 6 |

-continued

| No. | Structure | t_Ret (HPLC) [min] | MS (M + H)+ | PTK2 IC50 [nM] |
|---|---|---|---|---|
| 49 | 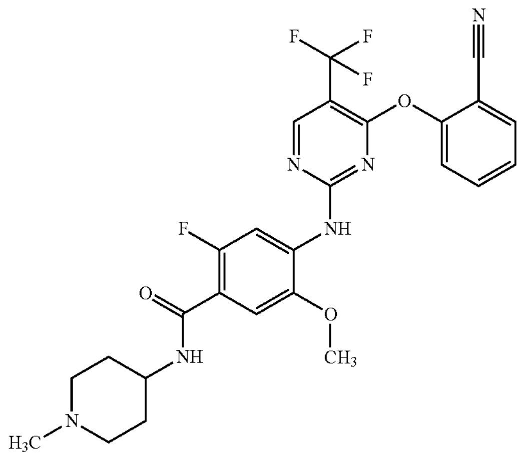 [SMILES: COc1cc(C(=O)NC2CCN(C)CC2)c(F)cc1Nc1ncc(C(F)(F)F)c(Oc2ccccc2C#N)n1] | 2.10 | 545 | 7 |
| 50 | 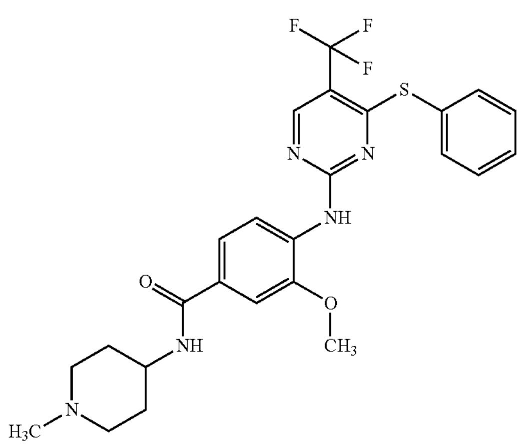 [SMILES: COc1cc(C(=O)NC2CCN(C)CC2)ccc1Nc1ncc(C(F)(F)F)c(Sc2ccccc2)n1] | 2.01 | 518 | 64 |

| No. | Structure | $t_{Ret}$(HPLC) [min] | MS (M + H)⁺ | PTK2 IC$_{50}$ [nM] |
|---|---|---|---|---|
| 51 | 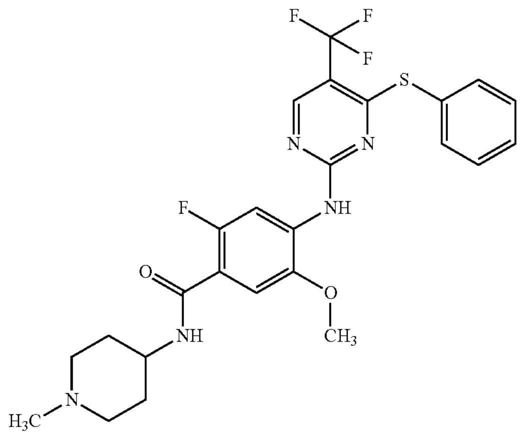 | 2.10 | 536 | 70 |

Example 52

3-methoxy-N-(1-methyl-piperidin-4-yl)-4-[4-((S)-1-methyl-pyrrolidin-2-ylmethoxy)-5-trifluoromethyl-pyrimidin-2-ylamino]-benzamide

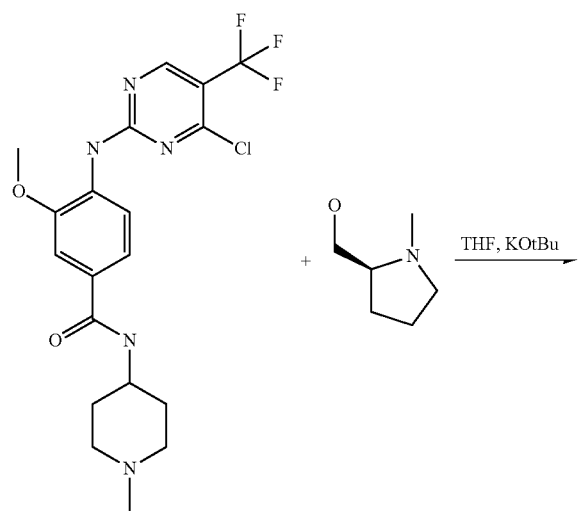

52

(S)-(−)-2-hydroxymethyl-1-methylpyrollidine (19.5 mg) is suspended in THF and at 0° C. a solution of KOtBu (1 mol/L in tBuOH, 0.29 mL) and (4-chloro-5-trifluoromethyl-pyrimidin-2-ylamino)-3-methoxy-N-(1-methyl-piperidin-4-yl)-benzamide (50 mg, see Example 1, step a) is added. After 30 min at RT more KOtBu (1 mol/L in tBuOH, 0.29 mL) is added and the reaction mixture is heated to 80° C. After 1 h the reaction mixture is diluted with EtOAc and washed 3× with 0.1 N HCl solution. The organic phase is dried on magnesium sulphate and evaporated down in vacuo. The final purification is carried out by preparative HPLC. (PTK2 IC$_{50}$=35 nmol).

The following compounds 53 to 84 are synthesised analogously, with the corresponding 4-chloro-5-trifluoromethylpyrimidines as educts:

Examples 53-84
| No. | Structure | $t_{Ret}$(HPLC) [min] | MS $(M + H)^+$ | PTK2 IC$_{50}$ [nM] |
|---|---|---|---|---|
| 53 | 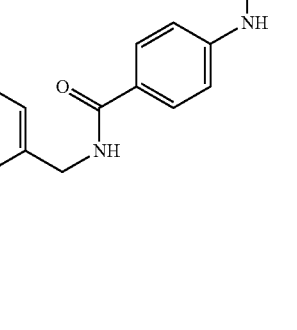 | 2.35 | 500 | 7852 |
| 54 | 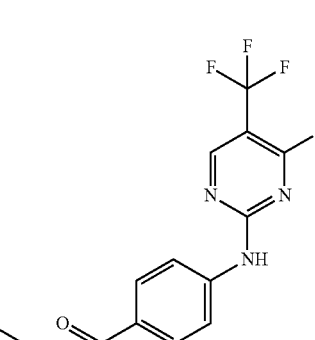 | 2.42 | 542 | 3054 |
| 55 | 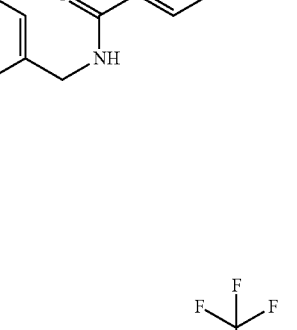 | 2.29 | 494 | 3295 |

-continued
| No. | Structure | $t_{Ret}$(HPLC) [min] | MS (M + H)$^+$ | PTK2 IC$_{50}$ [nM] |
|---|---|---|---|---|
| 56 | 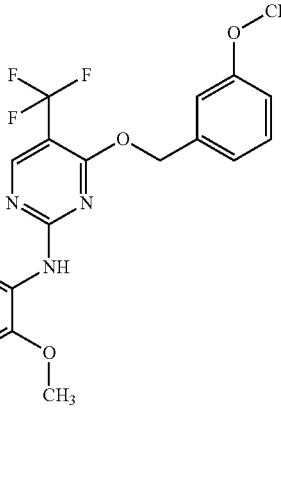 | 2.17 | 546 | 16 |
| 57 | 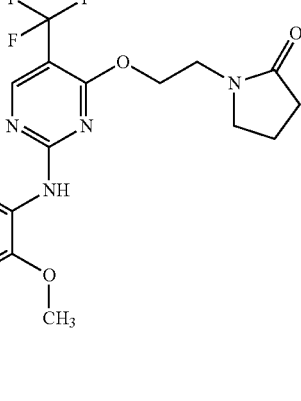 | 1.75 | 537 | 39 |
| 58 | 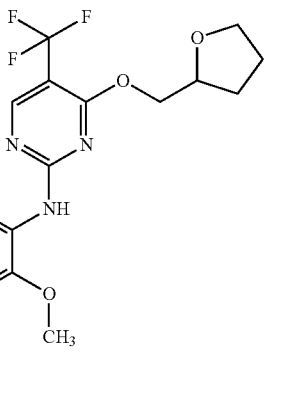 | 1.97 | 510 | 15 |

-continued

| No. | Structure | t_Ret (HPLC) [min] | MS (M + H)+ | PTK2 IC50 [nM] |
|---|---|---|---|---|
| 59 | 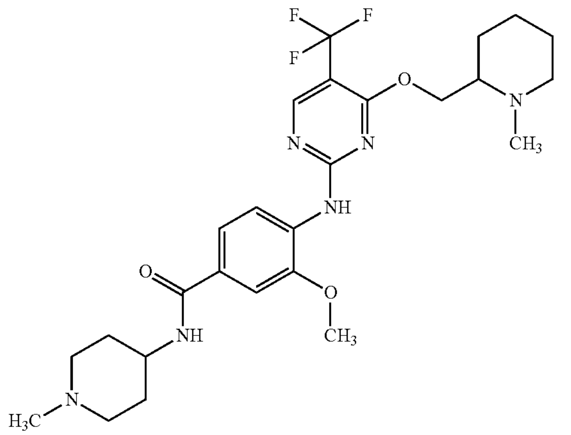 [SMILES: COc1cc(C(=O)NC2CCN(C)CC2)ccc1Nc1ncc(C(F)(F)F)c(OCC2CCCCN2C)n1] | 2.06 | 537 | 56 |
| 60 | 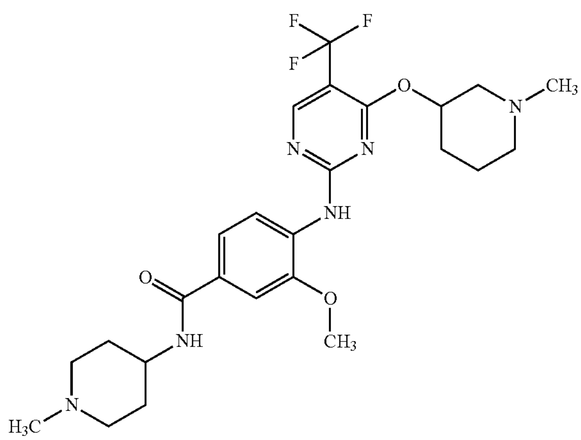 | 2.04 | 523 | 74 |
| 61 | 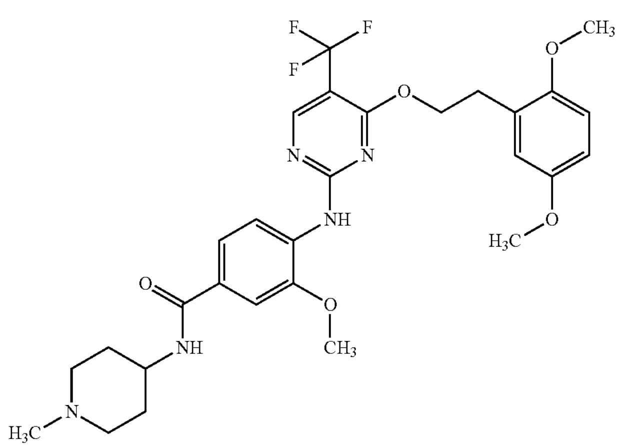 | 2.21 | 590 | 104 |

-continued

| No. | Structure | t_Ret (HPLC) [min] | MS (M + H)+ | PTK2 IC50 [nM] |
|---|---|---|---|---|
| 62 | 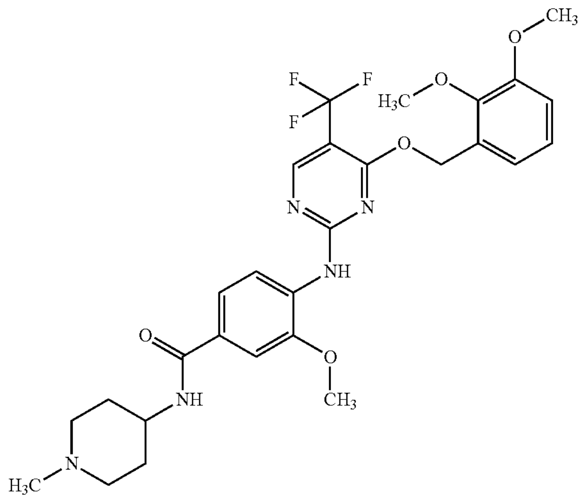 | 2.18 | 576 | 36 |
| 63 | 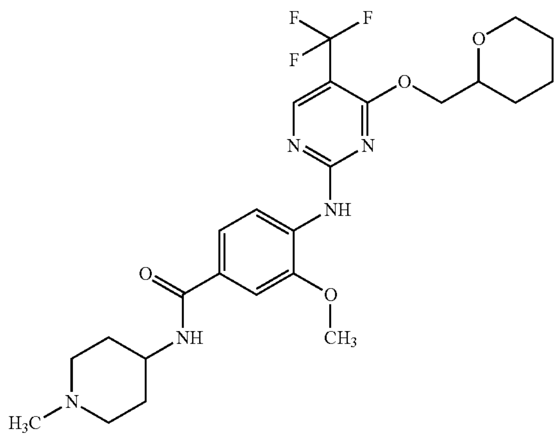 [SMILES: COc1cc(C(=O)NC2CCN(C)CC2)ccc1Nc1ncc(C(F)(F)F)c(OCC2CCCCO2)n1] | 2.10 | 524 | 40 |
| 64 | 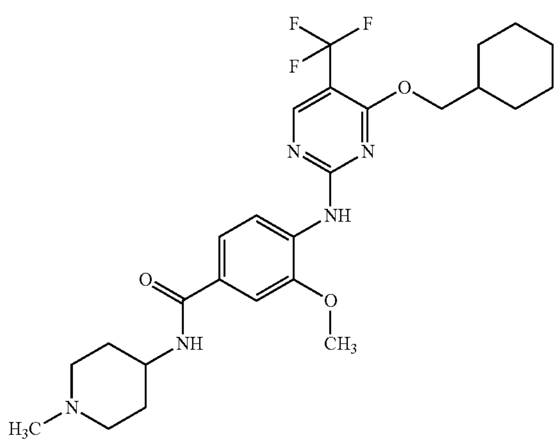 | 2.44 | 522 | 225 |

-continued

| No. | Structure | $t_{Ret}$ (HPLC) [min] | MS (M + H)$^+$ | PTK2 IC$_{50}$ [nM] |
|---|---|---|---|---|
| 65 | 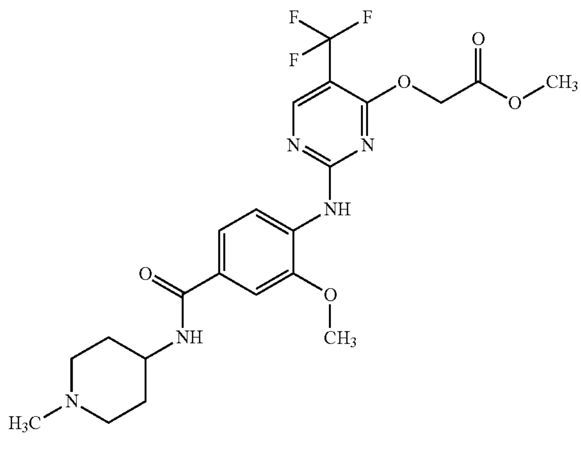 | 1.83 | 498 | 61 |
| 66 | 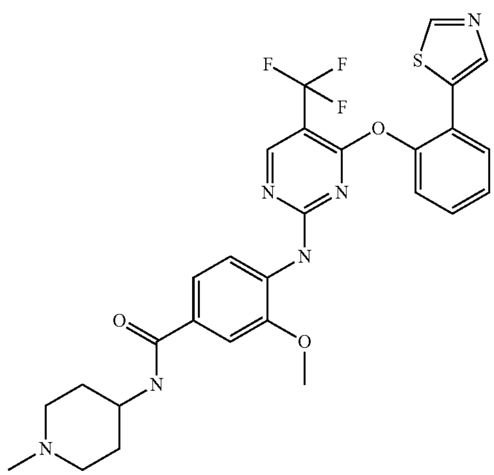 [SMILES: COc1cc(C(=O)NC2CCN(C)CC2)ccc1Nc1ncc(C(F)(F)F)c(Oc2ccccc2-c2cncs2)n1] | 1.92 | 585 | 222 |
| 67 | 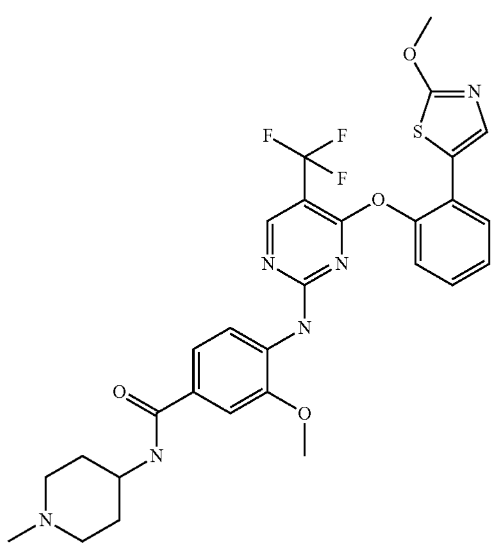 [SMILES: COc1ncc(-c2ccccc2Oc2nc(Nc3ccc(C(=O)NC4CCN(C)CC4)cc3OC)ncc2C(F)(F)F)s1] | 2.07 | 615 | 10000 |

-continued

| No. | Structure | t_Ret (HPLC) [min] | MS (M + H)+ | PTK2 IC50 [nM] |
|---|---|---|---|---|
| 68 | 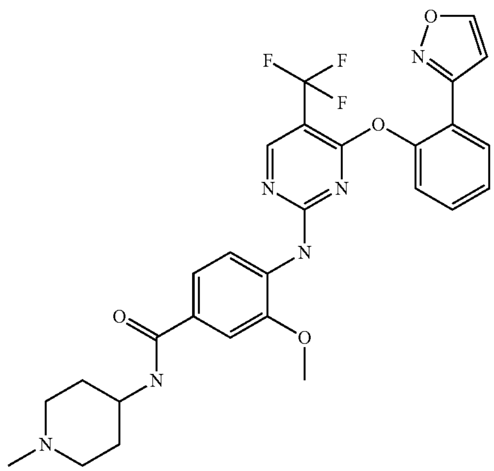 [SMILES: COc1cc(C(=O)NC2CCN(C)CC2)ccc1Nc1ncc(C(F)(F)F)c(Oc2ccccc2-c2ccon2)n1] | 1.92 | 569 | 19 |
| 69 | 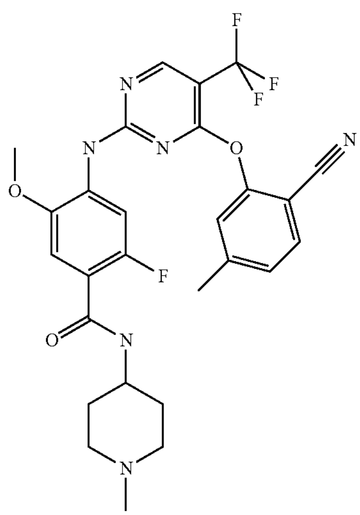 [SMILES: COc1cc(C(=O)NC2CCN(C)CC2)c(F)cc1Nc1ncc(C(F)(F)F)c(Oc2cc(C)ccc2C#N)n1] | 2.07 | 559 | 161 |
| 70 | 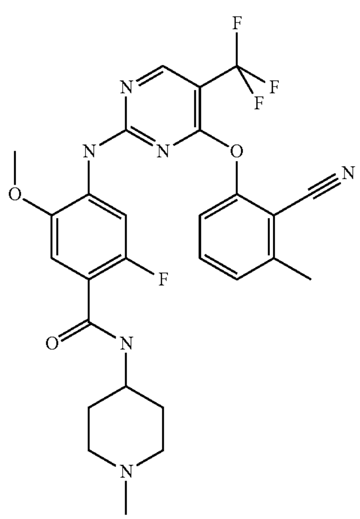 [SMILES: COc1cc(C(=O)NC2CCN(C)CC2)c(F)cc1Nc1ncc(C(F)(F)F)c(Oc2cccc(C)c2C#N)n1] | 2.05 | 559 | 9 |

-continued

| No. | Structure | t_Ret (HPLC) [min] | MS (M + H)+ | PTK2 IC_50 [nM] |
|---|---|---|---|---|
| 71 | 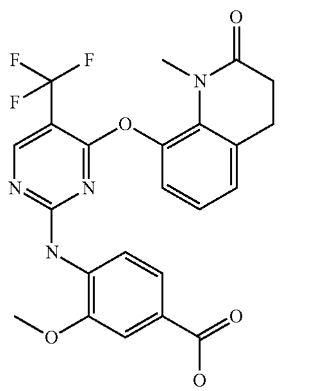 [SMILES: COc1cc(C(=O)O)ccc1Nc1ncc(C(F)(F)F)c(Oc2cccc3c2N(C)C(=O)CC3)n1] | 1.28 | 487 | 400 |
| 72 | 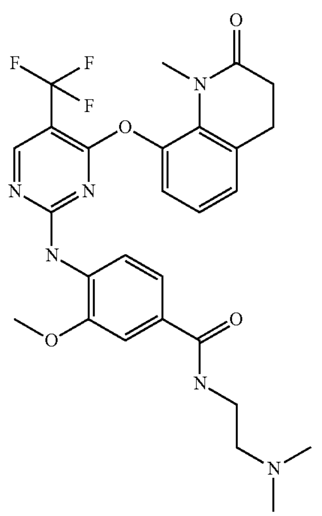 [SMILES: COc1cc(C(=O)NCCN(C)C)ccc1Nc1ncc(C(F)(F)F)c(Oc2cccc3c2N(C)C(=O)CC3)n1] | 1.90 | 559 | 127 |
| 73 | 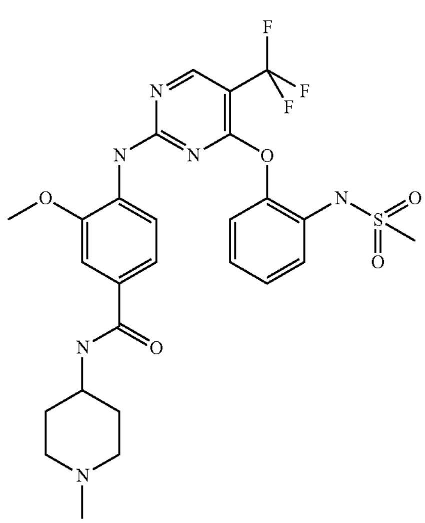 | 1.40 | 595 | 3 |

-continued

| No. | Structure | t_Ret (HPLC) [min] | MS (M + H)+ | PTK2 IC50 [nM] |
|---|---|---|---|---|
| 74 | 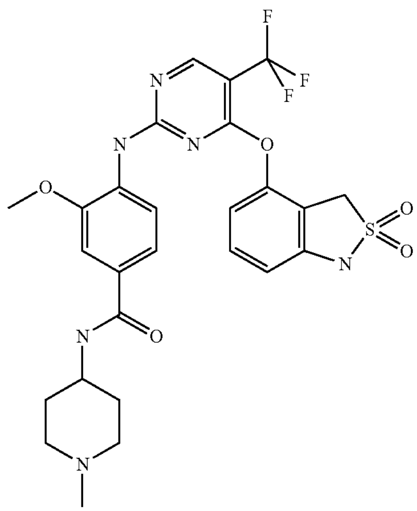 [SMILES: COc1cc(C(=O)NC2CCN(C)CC2)ccc1Nc1ncc(C(F)(F)F)c(Oc2cccc3c2CS(=O)(=O)N3)n1] | 1.30 | 593 | 365 |
| 75 | 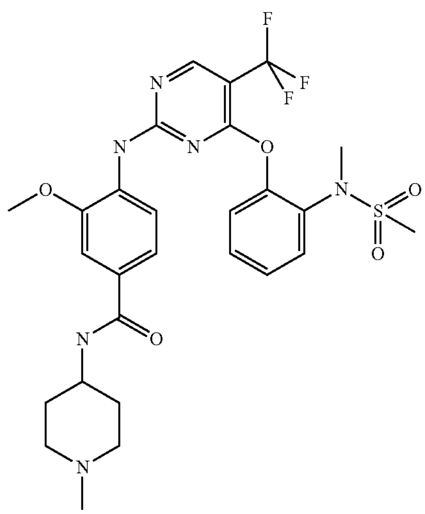 | 1.81 | 609 | 10 |
| 76 | 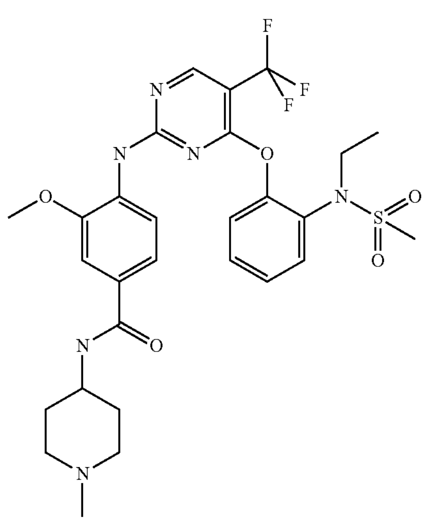 | 1.90 | 623 | 27 |

| No. | Structure | $t_{Ret}$ (HPLC) [min] | MS (M + H)$^+$ | PTK2 IC$_{50}$ [nM] |
|---|---|---|---|---|
| 77 | 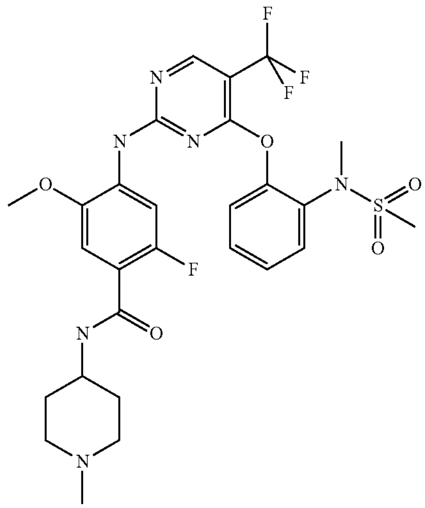 | 1.88 | 627 | 12 |
| 78 | 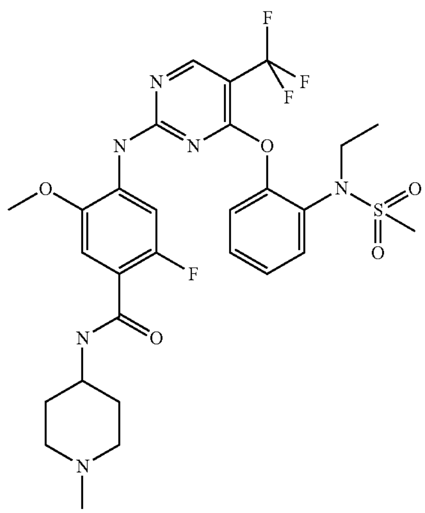 | 1.94 | 641 | 38 |
| 79 | 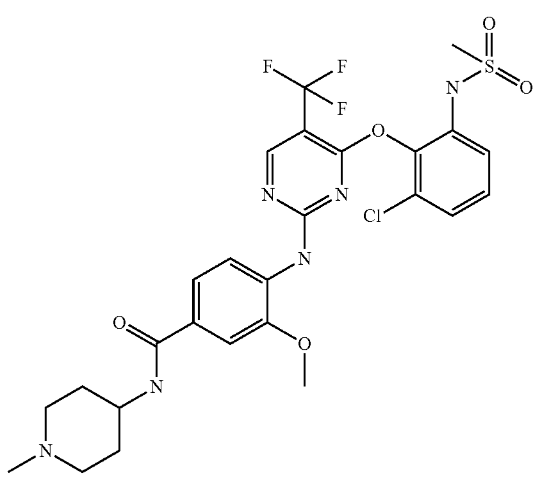 [SMILES: COc1cc(C(=O)NC2CCN(C)CC2)ccc1Nc1ncc(C(F)(F)F)c(Oc2c(Cl)cccc2NS(C)(=O)=O)n1] | 1.35 | 629 | 6 |

-continued

| No. | Structure | t$_{Ret}$(HPLC) [min] | MS (M + H)$^+$ | PTK2 IC$_{50}$ [nM] |
|---|---|---|---|---|
| 80 | 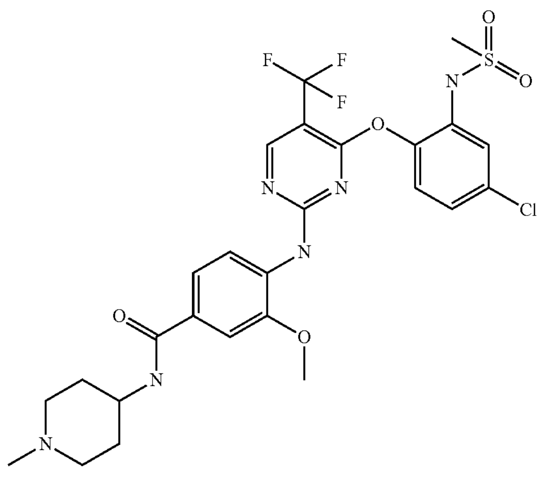 [SMILES: COc1cc(C(=O)NC2CCN(C)CC2)ccc1Nc1ncc(C(F)(F)F)c(Oc2ccc(Cl)cc2NS(C)(=O)=O)n1] | 1.35 | 629 | 10 |
| 81 | 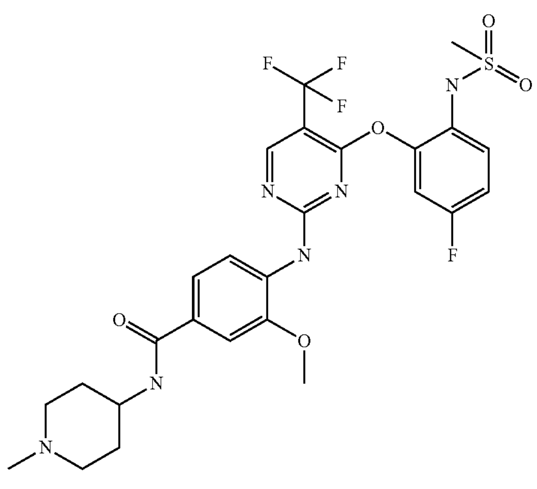 | 1.36 | 613 | 4 |
| 82 | 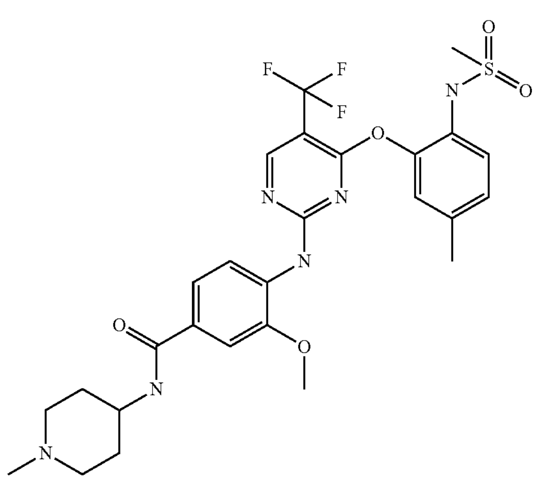 [SMILES: COc1cc(C(=O)NC2CCN(C)CC2)ccc1Nc1ncc(C(F)(F)F)c(Oc2cc(C)ccc2NS(C)(=O)=O)n1] | 1.56 | 609 | 12 |

| No. | Structure | t$_{Ret}$(HPLC) [min] | MS (M + H)$^+$ | PTK2 IC$_{50}$ [nM] |
|---|---|---|---|---|
| 83 | 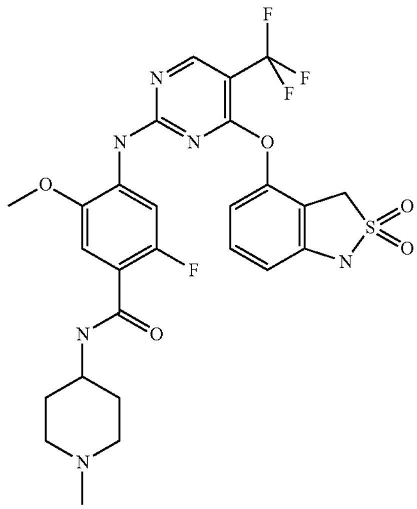 [SMILES: COc1cc(C(=O)NC2CCN(C)CC2)c(F)cc1Nc1ncc(C(F)(F)F)c(Oc2cccc3c2CS(=O)(=O)N3)n1] | 1.36 | 611 | 400 |
| 84 | 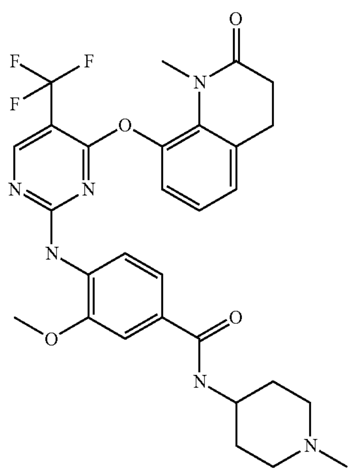 [SMILES: COc1cc(C(=O)NC2CCN(C)CC2)ccc1Nc1ncc(C(F)(F)F)c(Oc2cccc3c2N(C)C(=O)CC3)n1] | 1.90 | 585 | 245 |

The following Examples describe the biological activity of the compounds according to the invention without restricting the invention to these Examples.

PTK2 Enzyme Test

This test uses active PTK2 enzyme (Invitrogen Code PV3832) and poly-Glu-Tyr (4:1, Sigma P-0275) as the kinase substrate. The kinase activity is detected by means of the phosphorylation of the substrate in a DELFIA™ assay. The phosphorylated substrate is detected with the Europium-labelled phosphotyrosine antibody PY20 (Perkin Elmer, No.: AD0038).

In order to determine concentration-activity curves with PTK2-inhibitors the compounds are serially diluted in 10% DMSO/H$_2$O and 10 L of each dilution are dispensed per well in a 96-well microtitre plate (clear U-shaped base plate, Greiner No. 650101) (the inhibitors are tested in duplicates) and mixed with 10 L/well of PTK2 kinase (0.01 μg/well). PTK2 kinase is diluted accordingly beforehand with kinase dilution buffer (20 mM TRIS/HCl pH 7.5, 0.1 mM EDTA, 0.1 mM EGTA, 0.286 mM sodium orthovanadate, 10% glycerol with the addition of freshly prepared BSA (fraction V 1 mg/mL) and DTT (1 mM)). The test compound and the PTK2 kinase are pre-incubated for 1 h at RT and shaken at 500 rpm. Then 20 μL ATP Mix (30 mM TRIS/HCl pH 7.5, 0.02% Brij, 0.2 mM sodium orthovanadate, 10 mM magnesium acetate, 0.1 mM EGTA, 1× Phosphatase Inhibitor Cocktail 1 (Sigma, No.: P2850), 50 μM ATP (Sigma, No.: A3377; 15 mM stock solution)) are added. The reaction is started by the addition of 10 L/well of poly (Glu,Tyr) substrate (25 g/well poly (Glu, Tyr), 0.05 g/well biotinylated poly (Glu,Tyr) dissolved in 250 mM TRIS/HCl pH 7.5, 9 mM DTT)—the final concentration of DMSO is 2%. After 1 h kinase reaction (the plates are shaken at 500 rpm), the reaction is stopped by the addition of 12 μL/well of 100 mM EDTA, pH 8, and shaken for a further 5 min at RT (500 U/min).

55 μL of the reaction mixture are transferred into a streptavidin plate (Strepta Well High Bind (transparent, 96-well) made by Roche, No.: 11989685001) and incubated for 1 h at RT (shaking at 500 rpm). Then the microtitre plate is washed three times with 200 μL/well D-PBS (Invitrogen, No.: 14190). 100 μL of 1:2000 diluted DELFIA Eu-N1 Anti-Phosphotyrosine PY20 antibody (Perkin Elmer, No.: AD0038, 1:2000 diluted in DELFIA test buffer (Perkin Elmer, No.: 1244-111)) is then added and it is incubated for 1 h at RT (shaking at 500 rpm). Then the plate is washed three times with 200 μL/well DELFIA washing buffer (Perkin Elmer, No.: 1244-114), 200 µL/well strengthening solution (Perkin Elmer, No.: 1244-105) is added and the whole is incubated for 10 min at RT (shaking at 300 rpm).

The time-delayed Europium fluorescence is then measured in a microtitre plate reader (Victor, Perkin Elmer). The positive control consists of wells that contain solvent (2% DMSO in test buffer) and display uninhibited kinase activity. Wells that contain test buffer instead of enzyme act as a control for the background kinase activity.

The $IC_{50}$ values are determined from concentration-activity analyses by iterative calculation using a sigmoidal curve analysis algorithm (FIFTY, based on GraphPAD Prism Version 3.03) with a variable Hill coefficient.

Soft-Agar Assay

This cellular test is used to determine the influence of PTK2-inhibitors on the growth of PC-3 prostate carcinoma cells in soft agar ('anchorage-independent growth'). After an incubation time of two weeks the cell vitality is demonstrated by Alamar Blue (resazurin) staining.

PC-3 cells (ATCC CRL-1435) are grown in cell culture flasks (175 $cm^2$) with F12 Kaighn's Medium (Gibco, No.: 21127) which has been supplemented with 10% foetal calf serum (Invitrogen, No.: 16000-044). The cultures are incubated in the incubator at 37° C. and 5% $CO_2$ and are run twice a week. The test I carried out in microtitre plates (Greiner, No.: 655 185) and consists of a lower layer made up of 90 µL of medium with 1.2% agarose (Invitrogen, 4% agarose gel 1× liquid 40 mL, No.: 18300-012), followed by a cell layer in 60 µL medium and 0.3% agarose and finally a top layer comprising 30 µL medium which contains the test compounds (without the addition of agarose). To prepare the lower layer, 4% agarose are decocted with 10×D-PBS (Gibco, No.: 14200) and $H_2O$ and thus prediluted on 3% agarose in 1×D-PBS. The latter is adjusted with culture medium (F12 Kaighn's/10% FCS) and FCS to a final dilution of 1.2% agarose in F12 Kaighn's Medium with 10% FCS. Each well of a microtitre plate is supplied with 90 µL of the suspension for the lower layer and cooled to RT for 1 h. For the cell layer, PC-3 cells are detached using trypsin (Gibco, 0.05%; No.: 25300), counted and seeded in 60 µL F12 Kaighn's (10% FCS) with the addition of 0.3% agarose (37° C.). After cooling to RT for 1 h the test compounds (30 µL from serial dilutions) are added for quadruple measurements. The concentration of the test compounds usually covers a test range of between 10 µM and 0.3 nM. The compounds (stock solution: 10 mM in 100% DMSO) are prediluted in F12 Kaighn's Medium+6% DMSO, to obtain a final concentration of 1% DMSO. The cells are incubated at 37° C. and 5% $CO_2$ in a steam-saturated atmosphere for 14 days. The metabolic activity of living cells is then demonstrated with the dye Alamar Blue (AbD Serotec, No.: BUF012B). To do this, 18 µL/well of an Alamar Blue suspension are added and the whole is incubated for approx. 8 h in the incubator at 37° C. The positive control consists of empty wells that are filled with a mixture of 18 µL of Alamar Blue reduced by autoclaving and 180 µL of F12 Kaighn's Medium (10% FCS). The fluorescence intensity is determined by means of a fluorescence spectrometer (SpectraMAX GeminiXS, Molecular Devices). The excitation wavelength is 530 nm, the emission wavelength is 590 nm.

The $EC_{50}$ values are determined from concentrations-activity analyses by iterative calculation using a sigmoidal curve analysis algorithm (FIFTY, based on GraphPAD Prism Version 3.03) with a variable Hill coefficient.

Phospho-PTK2 (pY397) Assay

This cellular test is used to determine the influence of PTK2-inhibitors on the state of the PTK2-phosphorylation at tyrosine 397 (pY397).

PC-3 cells (prostate carcinoma, ATCC CRL-1435) are grown in cell culture flasks (175 $cm^2$) with F12 Kaighn's Medium (Gibco, No.: 21127) with the addition of 10% foetal calf serum (Invitrogen, No.: 16000-044). The cultures are incubated in the incubator at 37° C. and 5% $CO_2$ and run twice a week.

For the test, $2 \times 10^4$ cells pro well/90 µL medium are plated out in 96-well microtitre plates (Costar, No.: 3598) and incubated overnight in the incubator at 37° C. and 5% $CO_2$. The test compounds (10 µL from serial dilution) are added the next day. The concentration of the test compounds usually covers a range of 50 µM and 0.8 nM. The test compounds (stock solution: 10 mM in 100% DMSO) are diluted in medium/medium 10% DMSO such that the final concentration is 1% DMSO. The cells are then incubated in the incubator at 37° C. and 5% $CO_2$ for 2 h. Then the culture supernatant is removed and the cells are fixed with 150 µL 4% formaldehyde in D-PBS for 20 min at RT. The cell lawn is washed five times with 200 µL 0.1% Triton X-100 in D-PBS for 5 min in each case and then incubated for 90 min with blocking buffer (5% skimmed milk powder (Maresi Fixmilch) in TBST (25 mM Tris/HCl, pH 8.0, 150 mM NaCl, 0.05% Tween 20). The blocking buffer is replaced by 50 µL of the first antibody anti-phospho PTK2 [pY397] rabbit monoclonal (Invitrogen/Biosource, No.: 44-625G), which is diluted 1:200 in blocking buffer. For control purposes, alternatively a PTK2 [total] antibody (clone 4.47 mouse monoclonal, Upstate, No.: 05-537), diluted 1:400 in blocking buffer is used. This incubation is carried out at 4° C. overnight. Then the cell lawn is washed five times with 100 µL of 0.1% Tween in D-PBS for 5 min in each case and 50 L/well of second antibody are added. In order to detect bound phospho-PTK2 [pY397] antibody a goat-anti-rabbit antibody is used which is coupled with horseradish peroxidase (Dako, No.: P0448; 1:500 dilution in blocking buffer). In order to detect bound PTK2 [total]-antibodies a rabbit-anti-mouse antibody is used, which is also coupled with horseradish peroxidase (Dako, No.: PO161; 1:1000 dilution in blocking buffer). This incubation is carried out for 1 h at RT with gentle shaking. The cell lawn is then again washed five times with 100 µL of 0.1% Tween in D-PBS for 5 min in each case. Peroxidase staining is carried out by adding 100 µL staining solution (1:1 mixture of TMB peroxidase substrate (KPL, No.: 50-76-02) and peroxidase solution B ($H_2O_2$) (KPL, No.: 50-65-02). The development of the stain takes place for 10-30 min in the dark. The reaction is stopped by the addition of 100 µL/well of a 1 M phosphoric acid solution. The absorption is determined photometrically at 450 nm with an absorption measuring device (VICTOR$^3$ PerkinElmer). The inhibition of the anti-phospho PTK2 [pY397] immune staining is used to determine $EC_{50}$ values. The staining with anti-PTK2 [total]-antibodies is for control purposes and should remain constant under the influence of inhibitor. The $EC_{50}$ values are determined from concentration-activity analyses by iterative calculation with the aid of a sigmoidal curve analysis algorithm (FIFTY, based on GraphPAD Prism Version 3.03) with a variable Hill coefficient.

The substances of the present invention are PTK2-kinase inhibitors. In view of their biological properties the new compounds of general formula (1), the isomers thereof and the physiologically acceptable salts thereof are suitable for the treatment of diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto:

brain tumours such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumour such as prolactinoma, hypophyseal incidentaloma, HGH (human growth hormone) producing adenoma and corticotrophic adenoma, craniopharyngiomas, medulloblastoma, meningeoma and oligodendroglioma; nerve tumours such as for example tumours of the vegetative nervous system such as neuroblastoma, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus and duodenum; eyelid tumours (basalioma or adenocarcinoma of the eyelid apparatus); retinoblastoma; carcinoma of the pancreas; carcinoma of the bladder; lung tumours (bronchial carcinoma—small-cell lung cancer (SCLC), non-small-cell lung cancer (NSCLC) such as for example spindle-cell plate epithelial carcinomas, adenocarcinomas (acinary, paillary, bronchiolo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukaemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma—mucinous or serous cystoma, endometriodal tumours, clear cell tumour, Brenner's tumour); gall bladder cancer; bile duct cancer such as for example Klatskin tumour; testicular cancer (germinal or non-germinal germ cell tumours); laryngeal cancer such as for example supra-glottal, glottal and subglottal tumours of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumour, Ewing's sarcoma, and plasmocytoma, head and neck tumours (HNO tumours) such as for example tumours of the lips, and oral cavity (carcinoma of the lips, tongue, oral cavity), nasopharyngeal carcinoma (tumours of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumours of the paranasal sinuses and nasal cavity, tumours of the salivary glands and ears; liver cell carcinoma (hepatocellular carcinoma (HCC); leukaemias, such as for example acute leukaemias such as acute lymphatic/lymphoblastic leukaemia (ALL), acute myeloid leukaemia (AML); chronic lymphatic leukaemia (CLL), chronic myeloid leukaemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumour); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, lapatinib and trastuzumab); signal transduction inhibitors (e.g. imatinib and sorafenib); antimetabolites (e.g. antifolates such as methotrexate, premetrexed and raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions, —particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound selected from the group consisting of:

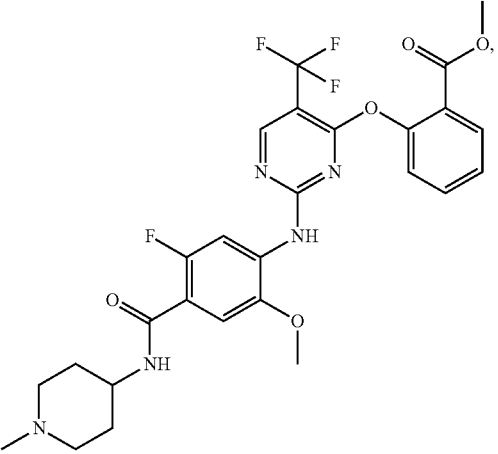

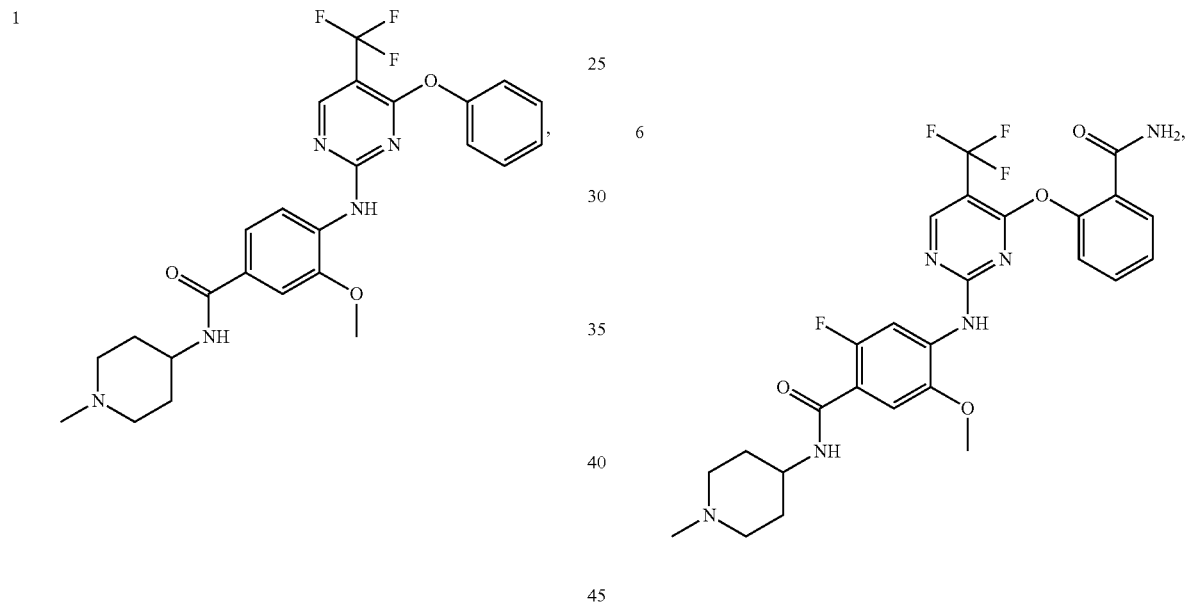

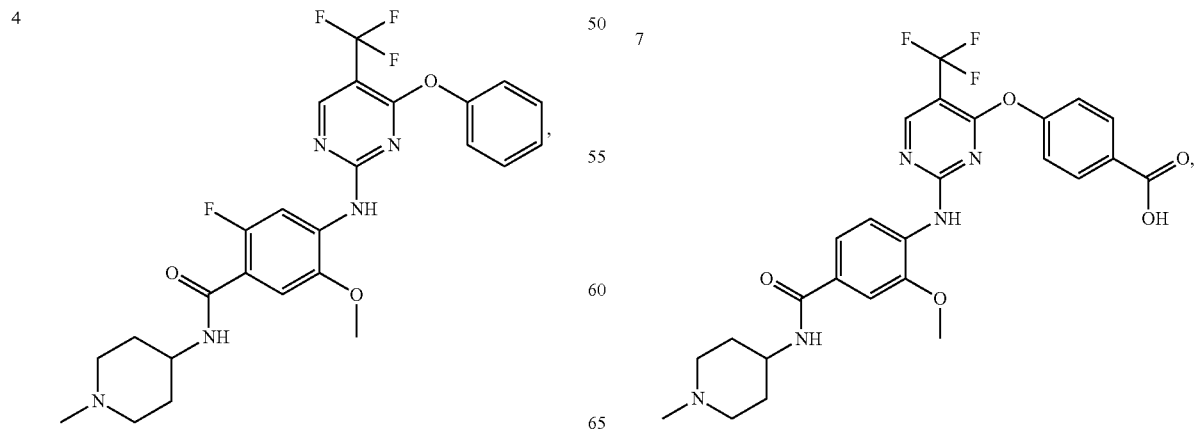

| 8 | 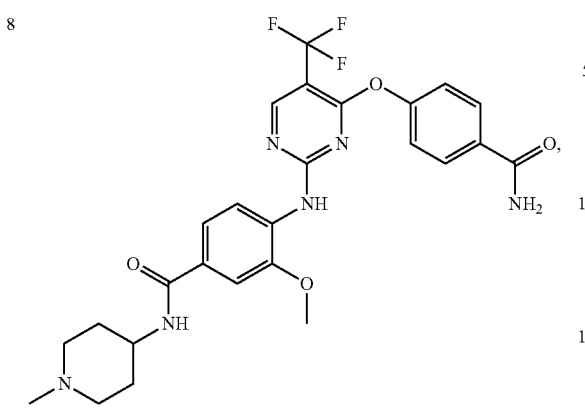 | 11 | 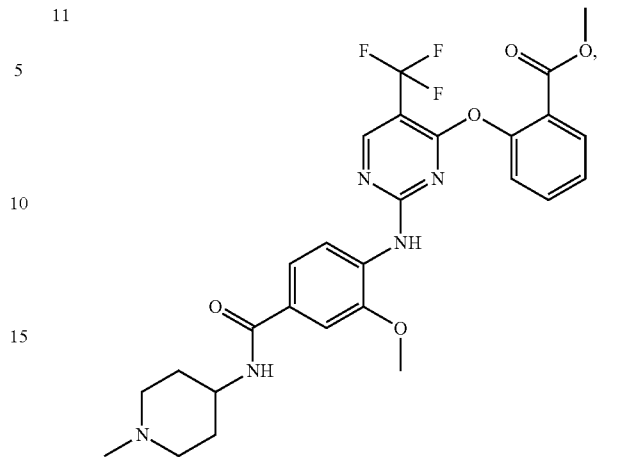 |
| 9 | 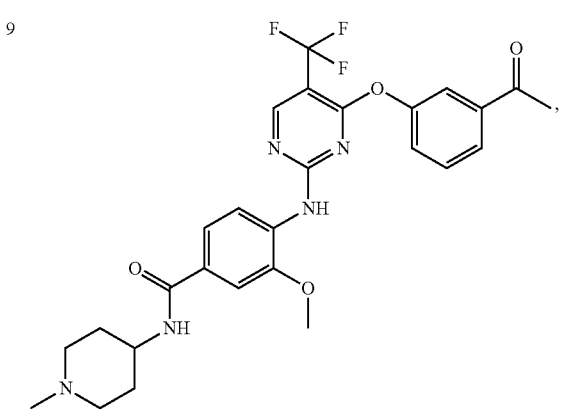 | 12 | 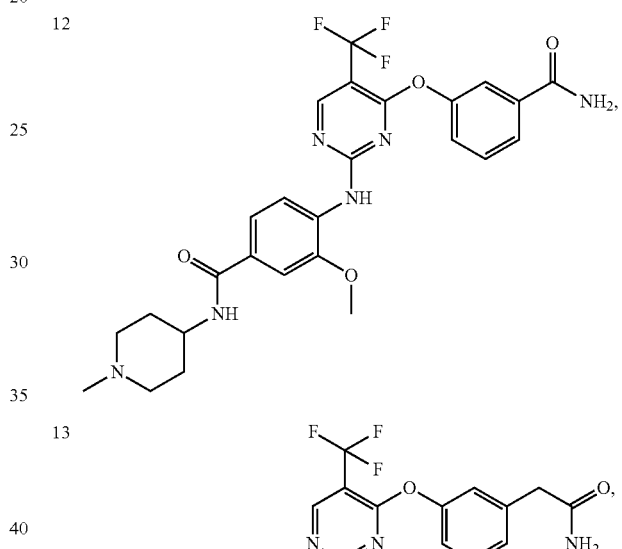 |
| | | 13 | |
| 10 | 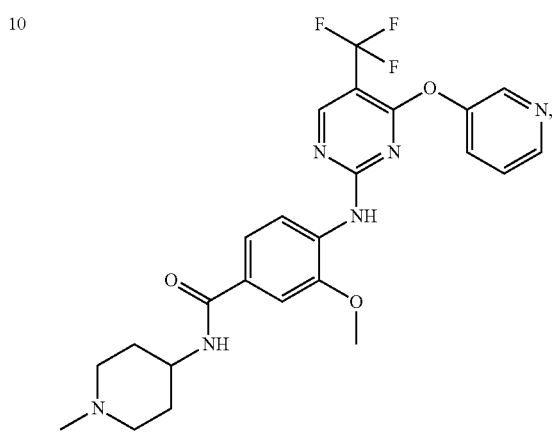 | 14 | 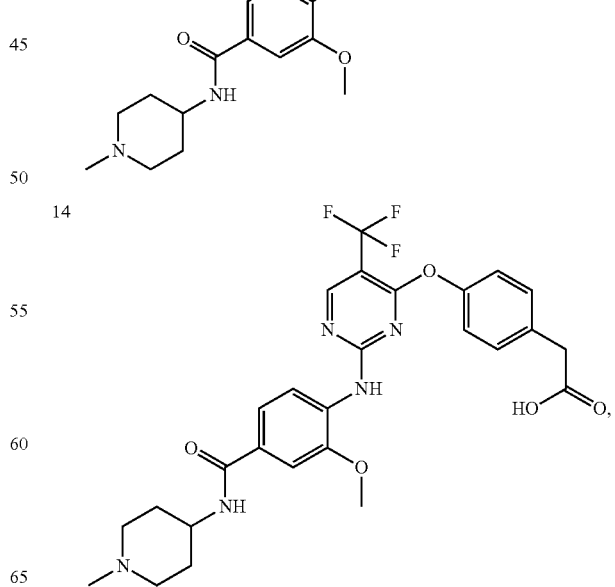 |

15 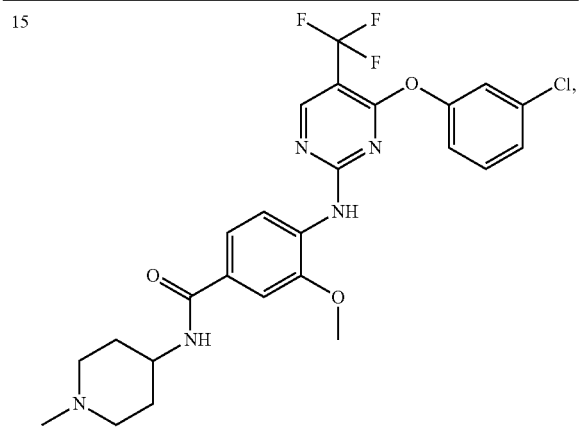
16 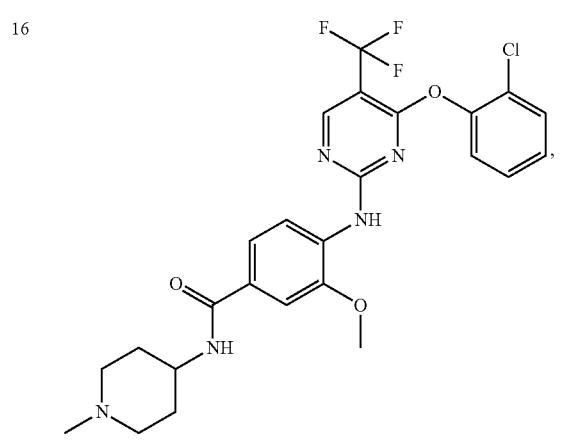
17 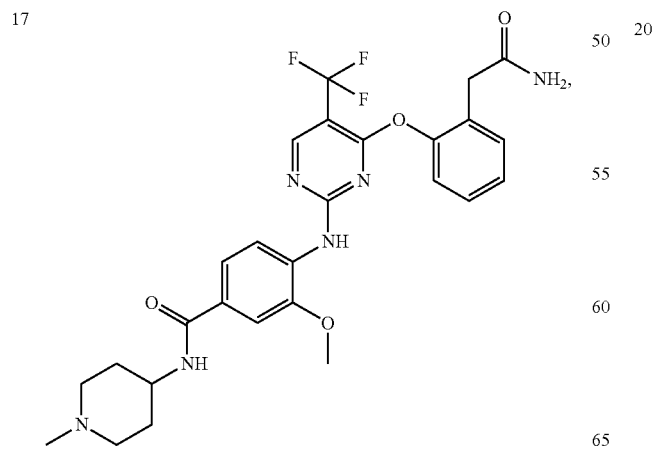
18 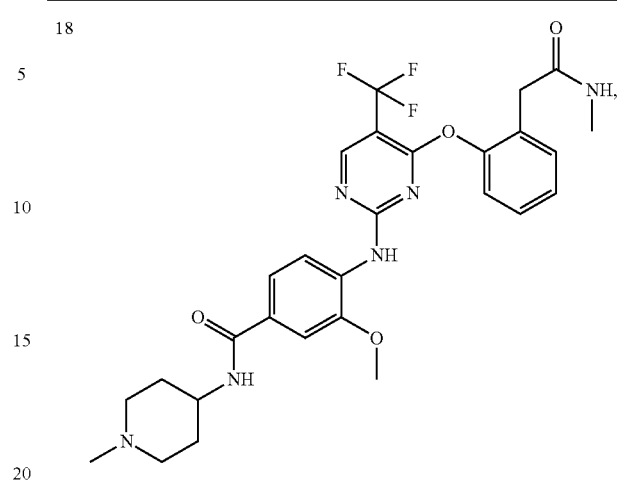
19 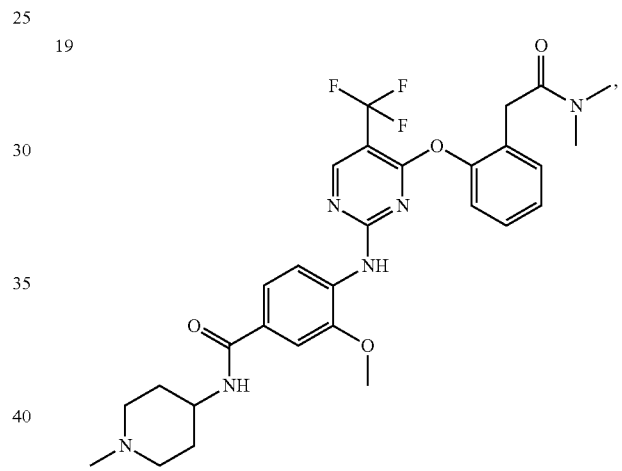
20 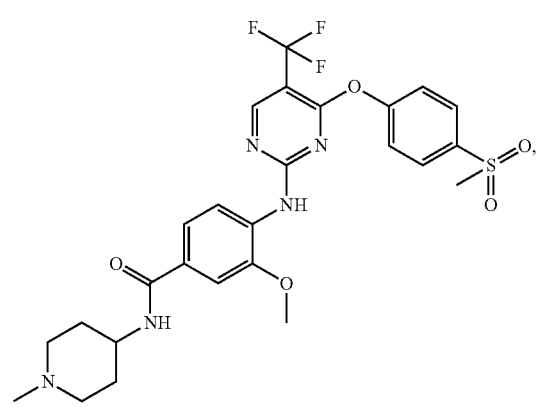 [SMILES: COc1cc(C(=O)NC2CCN(C)CC2)ccc1Nc1ncc(C(F)(F)F)c(Oc2ccc(S(C)(=O)=O)cc2)n1]

| 24 | 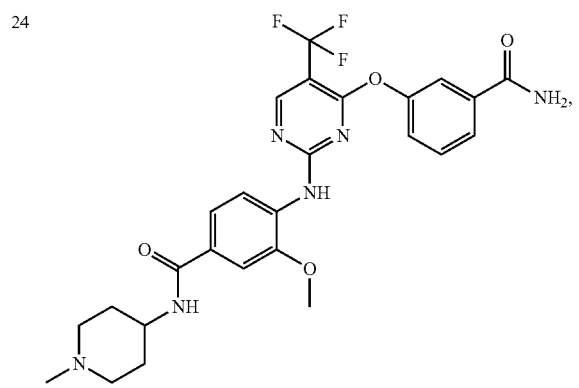 | 28 | 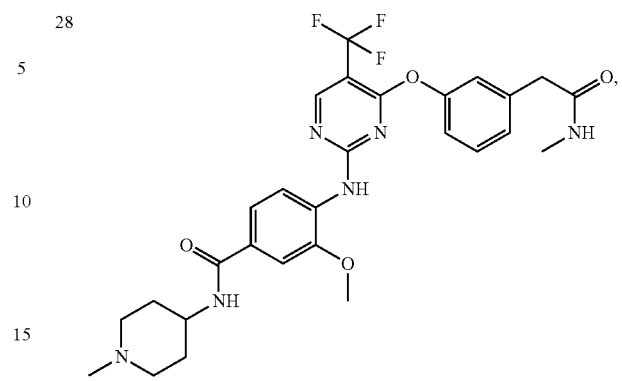 |
| 25 | 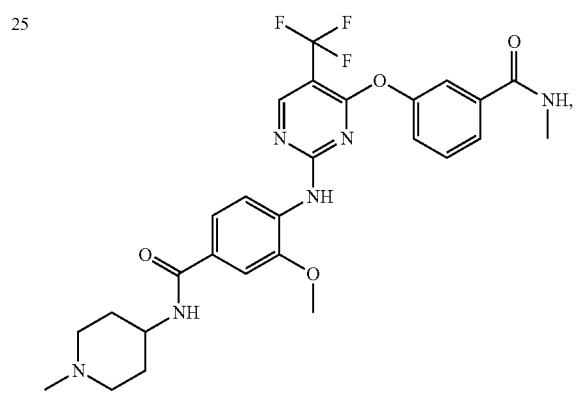 | 29 | 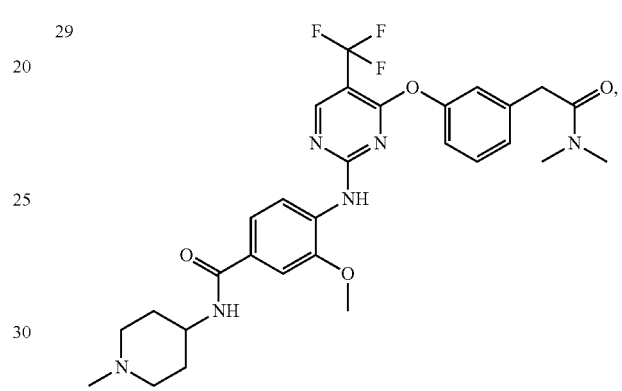 |
| 26 | 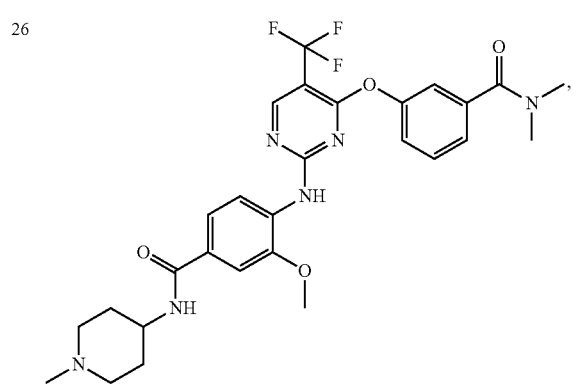 | 30 | 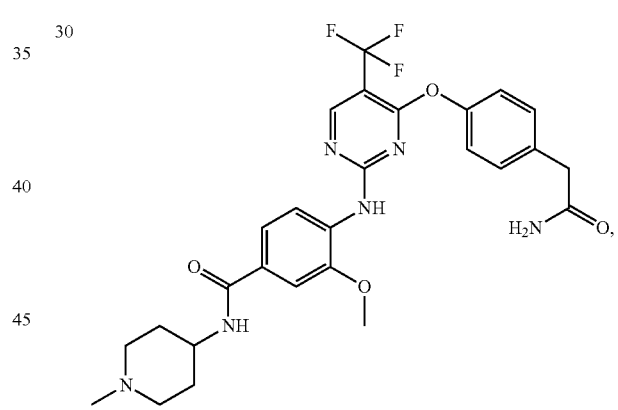 |
| 27 | 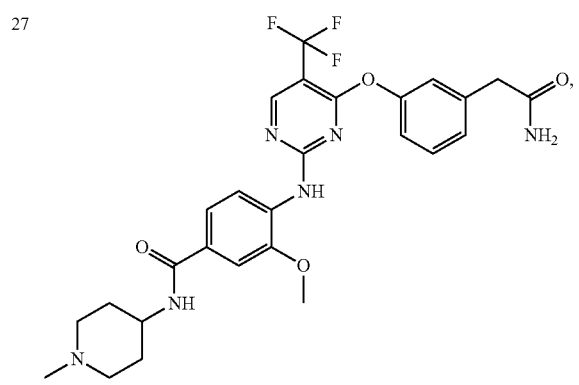 | 31 | 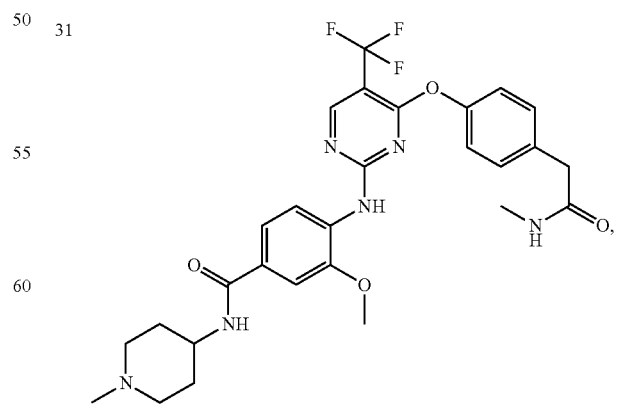 |

| 32 | 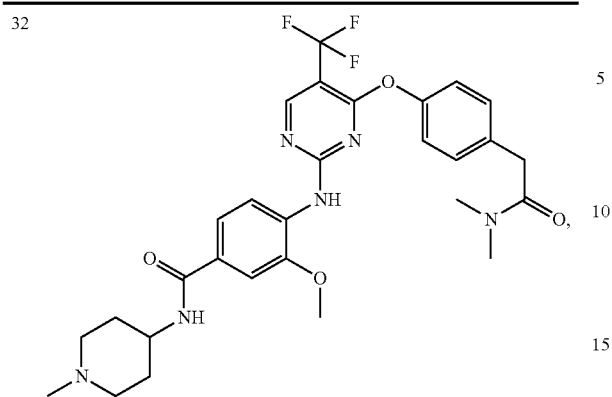 | 36 | 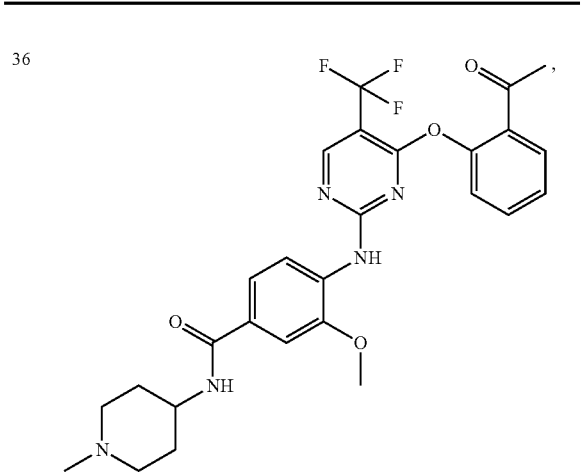 |
| 33 | 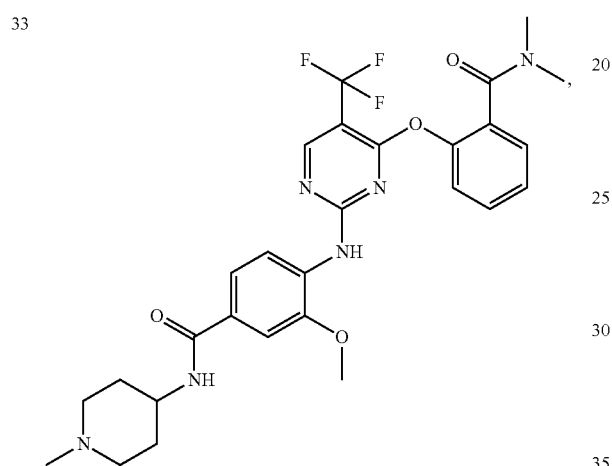 | 37 | 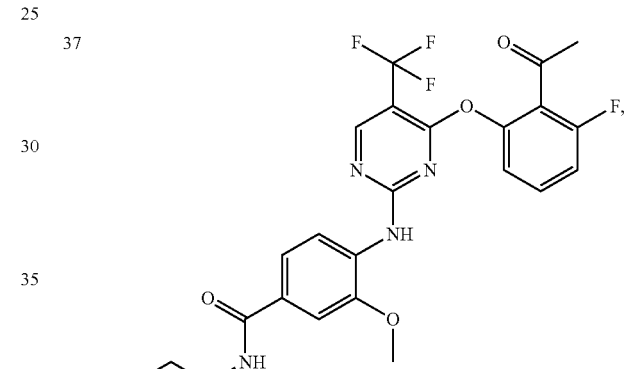 |
| 34 | 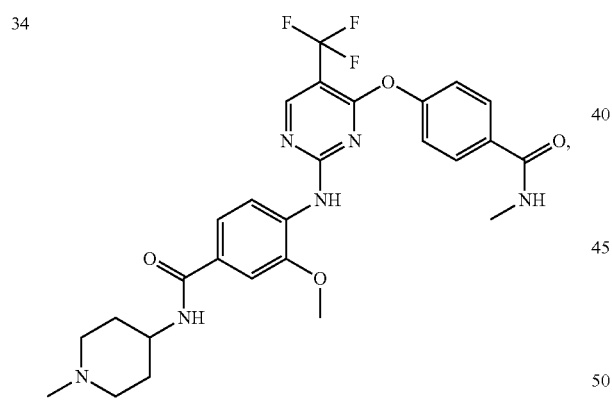 | 38 | 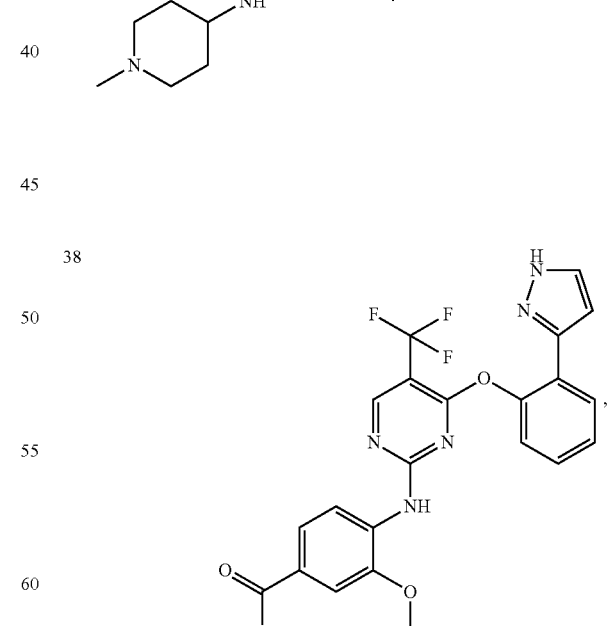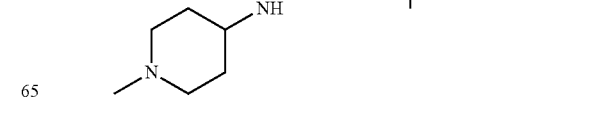 |
| 35 | 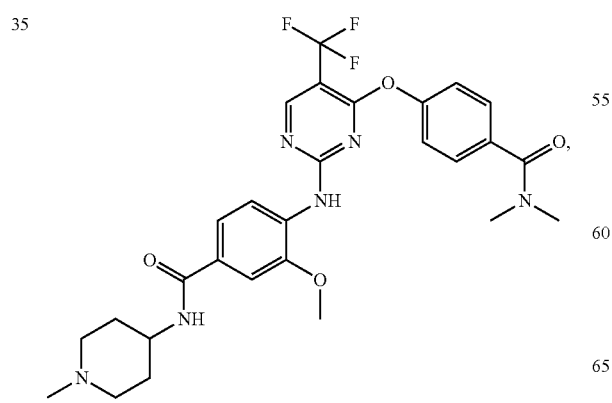 | | |

| 99 -continued | 100 -continued |
|---|---|
| 39 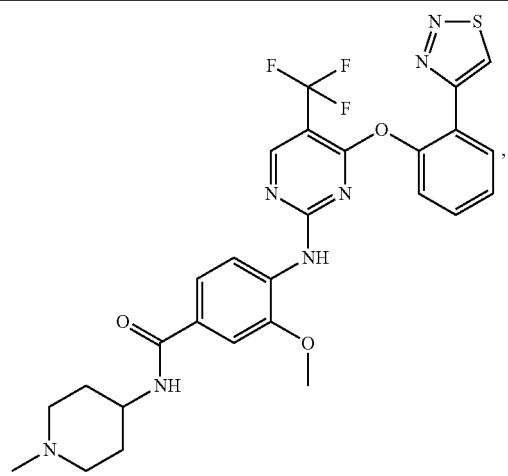 | 42 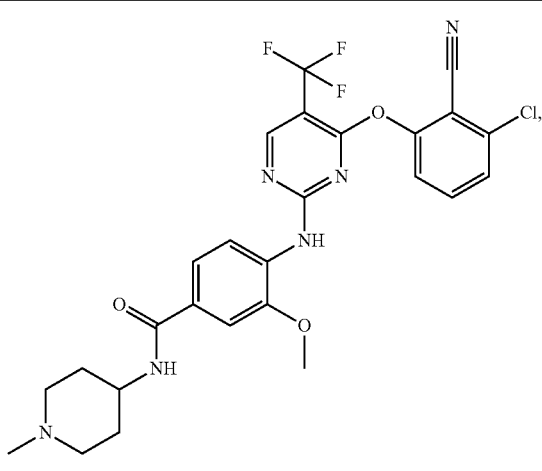 |
| 40 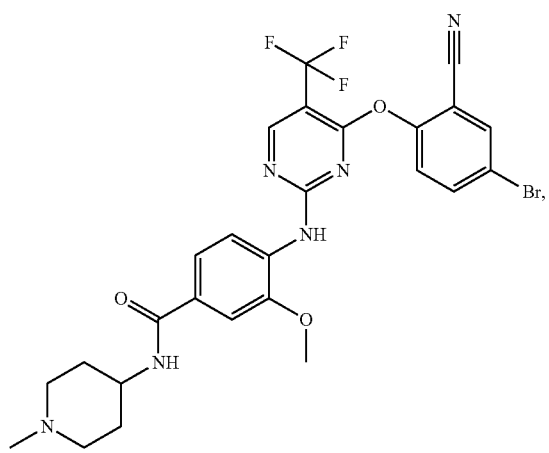 [SMILES: COc1cc(C(=O)NC2CCN(C)CC2)ccc1Nc1ncc(C(F)(F)F)c(Oc2ccc(Br)cc2C#N)n1] | 43 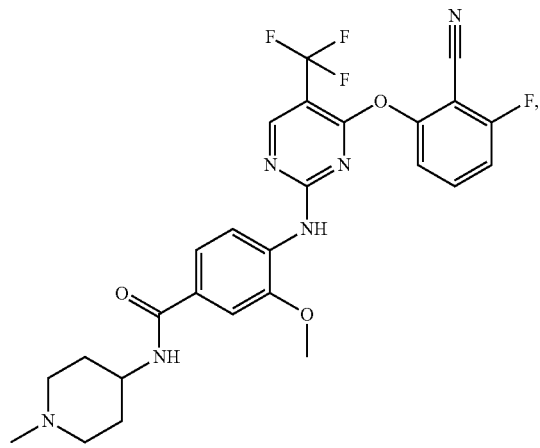 [SMILES: COc1cc(C(=O)NC2CCN(C)CC2)ccc1Nc1ncc(C(F)(F)F)c(Oc2cccc(F)c2C#N)n1] |
| 41 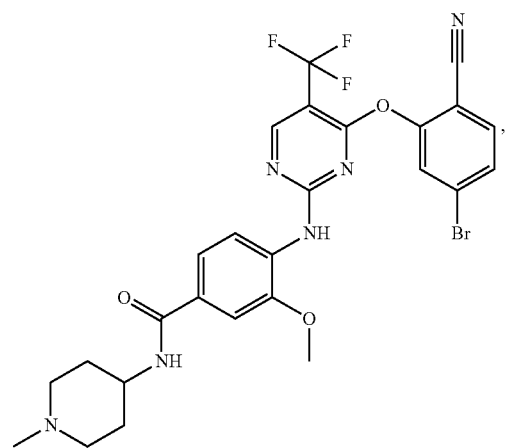 | 44 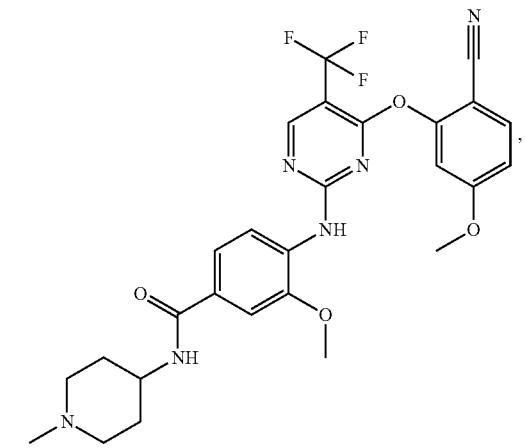 [SMILES: COc1ccc(C#N)c(Oc2nc(Nc3ccc(C(=O)NC4CCN(C)CC4)cc3OC)ncc2C(F)(F)F)c1] |

101
-continued
45
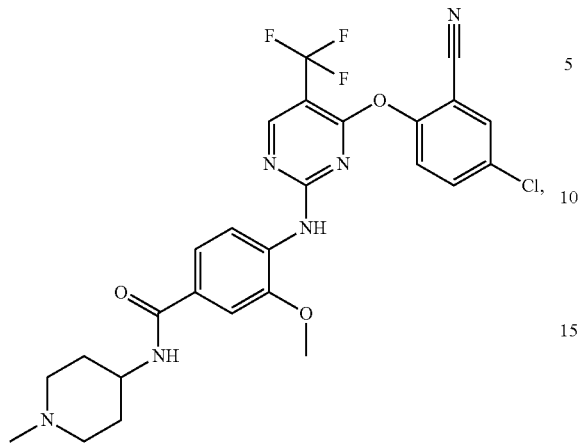
48
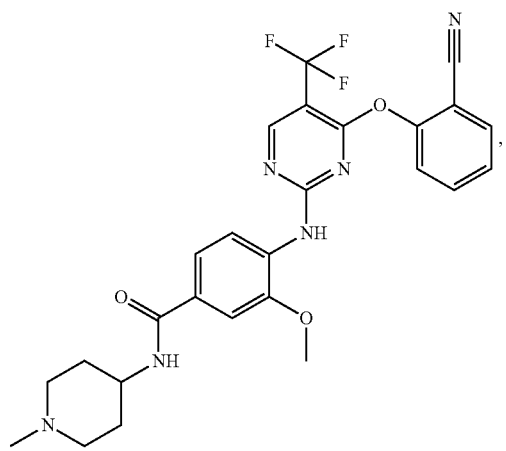 [SMILES: COc1cc(C(=O)NC2CCN(C)CC2)ccc1Nc1ncc(C(F)(F)F)c(Oc2ccccc2C#N)n1]
49
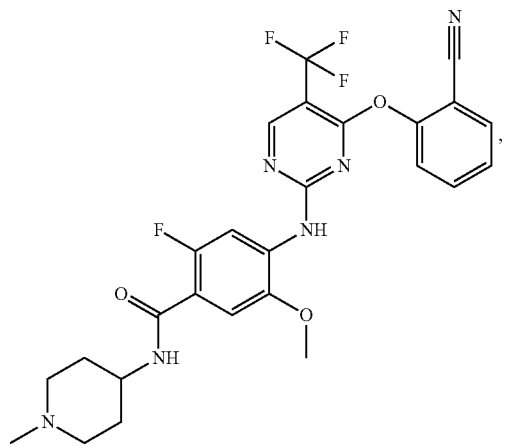 [SMILES: COc1cc(C(=O)NC2CCN(C)CC2)c(F)cc1Nc1ncc(C(F)(F)F)c(Oc2ccccc2C#N)n1]
102
-continued
50
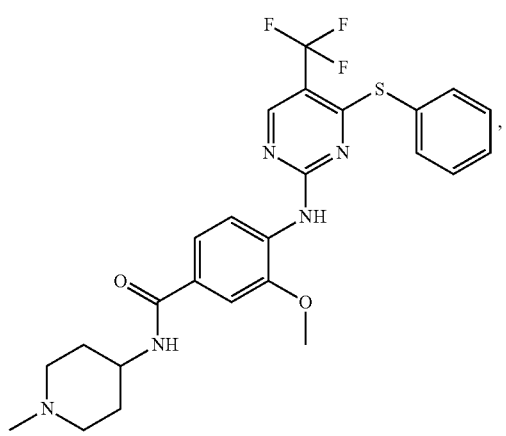 [SMILES: COc1cc(C(=O)NC2CCN(C)CC2)ccc1Nc1ncc(C(F)(F)F)c(Sc2ccccc2)n1]
51
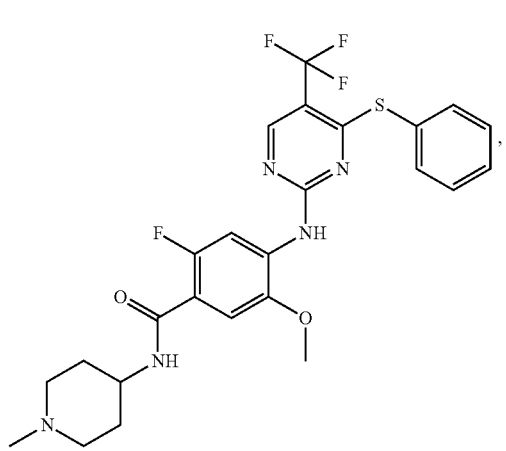 [SMILES: COc1cc(C(=O)NC2CCN(C)CC2)c(F)cc1Nc1ncc(C(F)(F)F)c(Sc2ccccc2)n1]
52
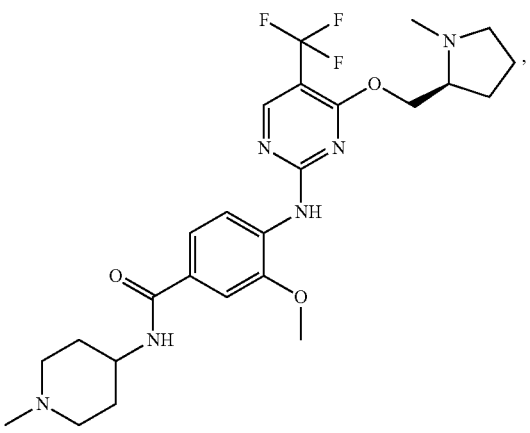 [SMILES: COc1cc(C(=O)NC2CCN(C)CC2)ccc1Nc1ncc(C(F)(F)F)c(OC[C@@H]2CCCN2C)n1]

| 56 | 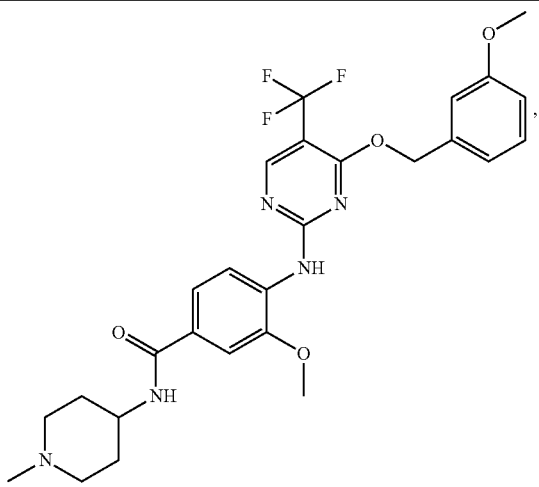 | 59 | 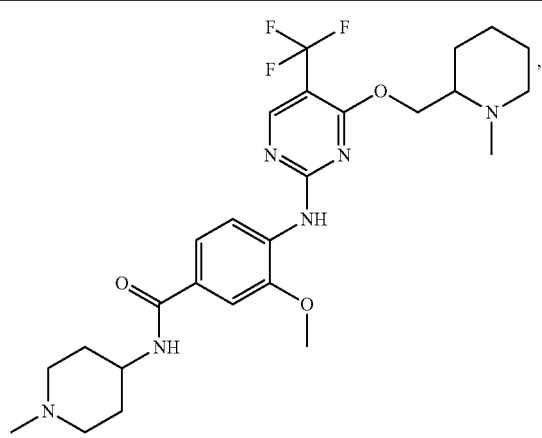 |
| --- | --- | --- | --- |
| 57 | 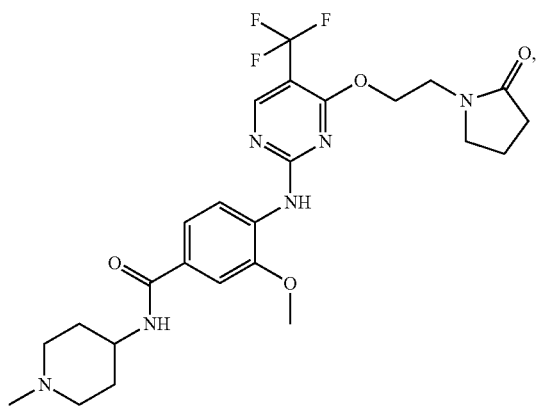 [SMILES: COc1cc(C(=O)NC2CCN(C)CC2)ccc1Nc1ncc(C(F)(F)F)c(OCCN2CCCC2=O)n1] | 60 | |
| 58 | 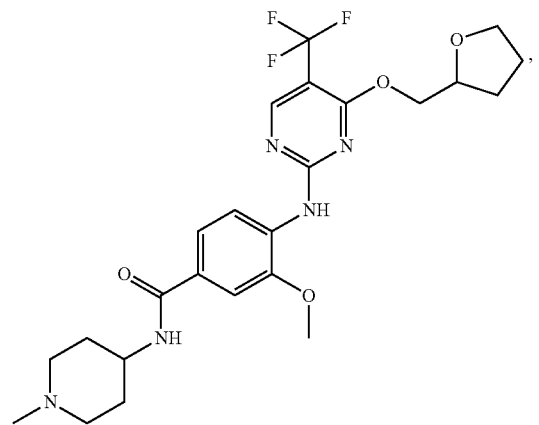 [SMILES: COc1cc(C(=O)NC2CCN(C)CC2)ccc1Nc1ncc(C(F)(F)F)c(OCC2CCCO2)n1] | 61 | 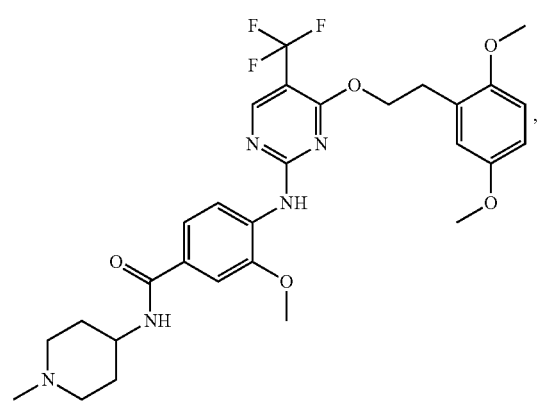 |

| 62 | 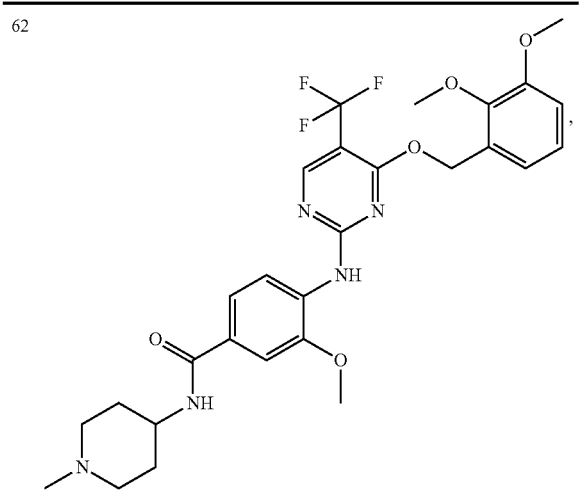 | 65 | 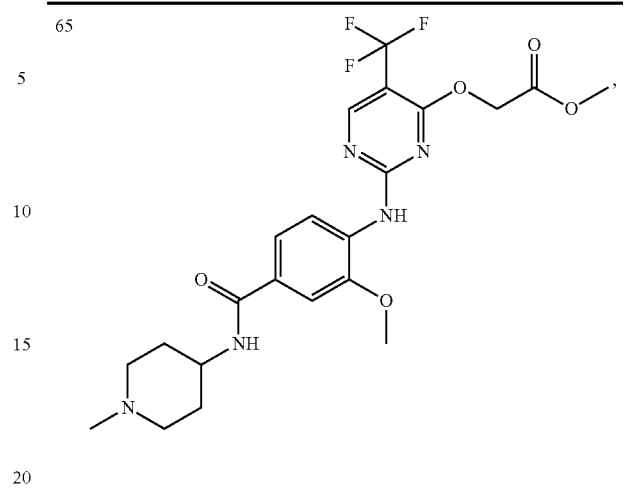 |
| --- | --- | --- | --- |
| 63 | 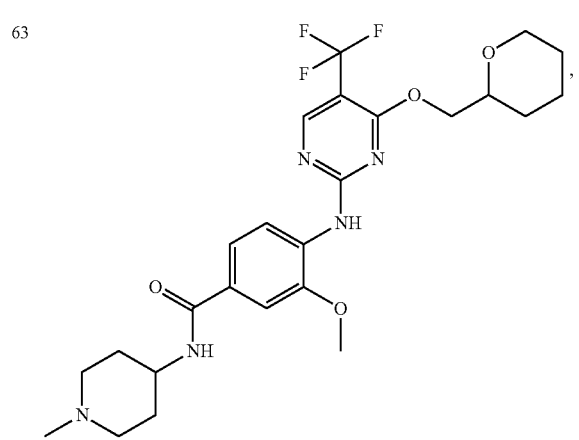 | 66 | 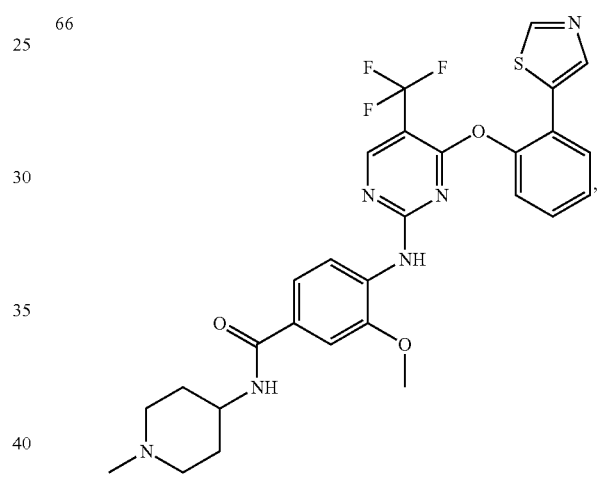 |
| 64 | 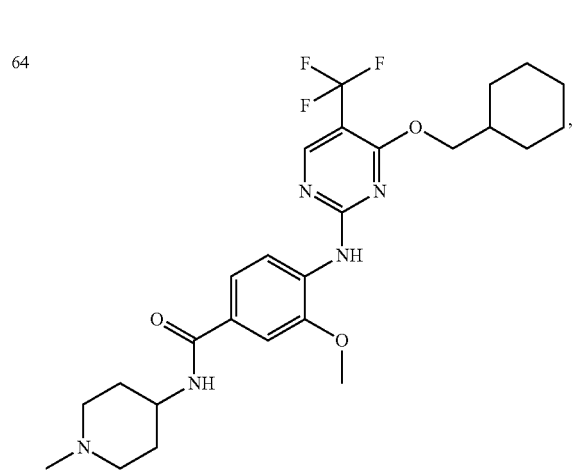 | 68 | 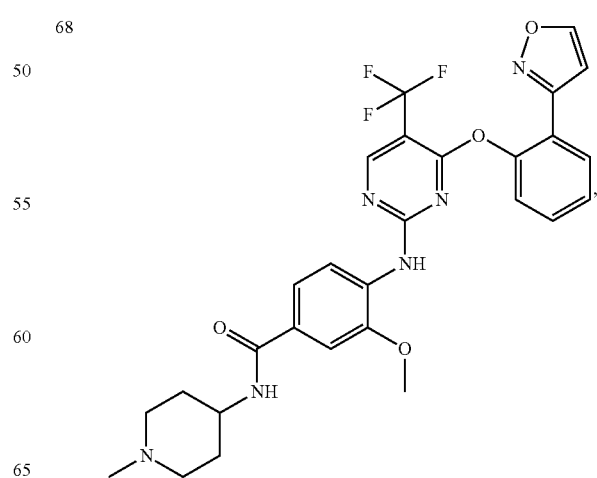 |

69 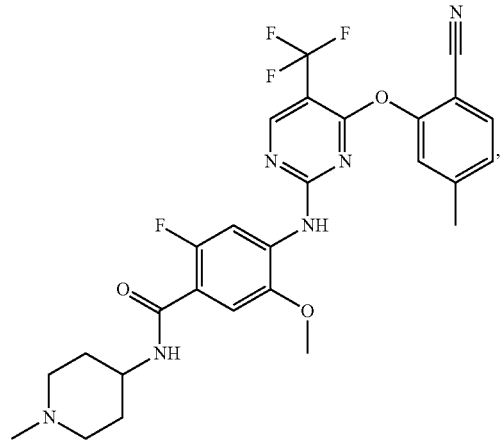 [SMILES: COc1cc(C(=O)NC2CCN(C)CC2)c(F)cc1Nc1ncc(C(F)(F)F)c(Oc2cc(C)ccc2C#N)n1]
70 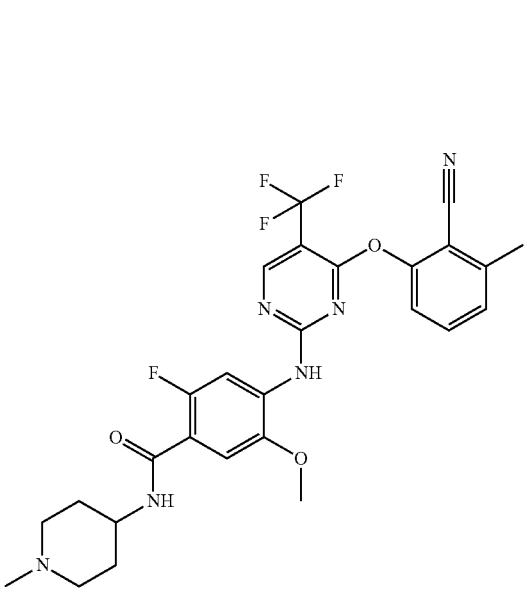
73 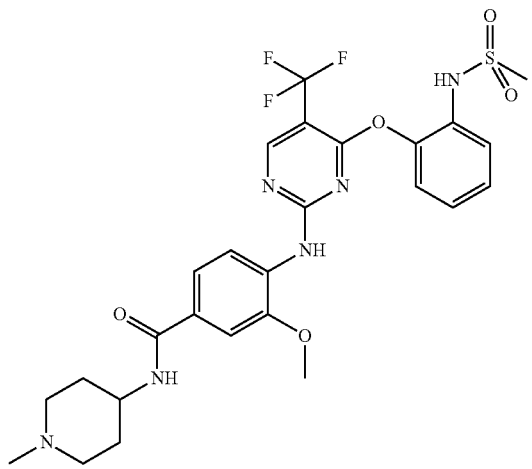
75 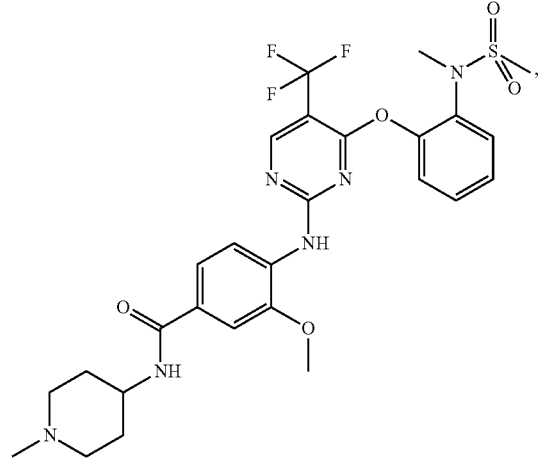
76 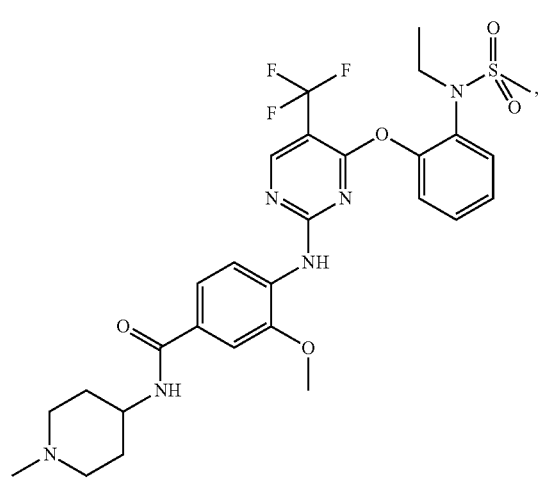
77 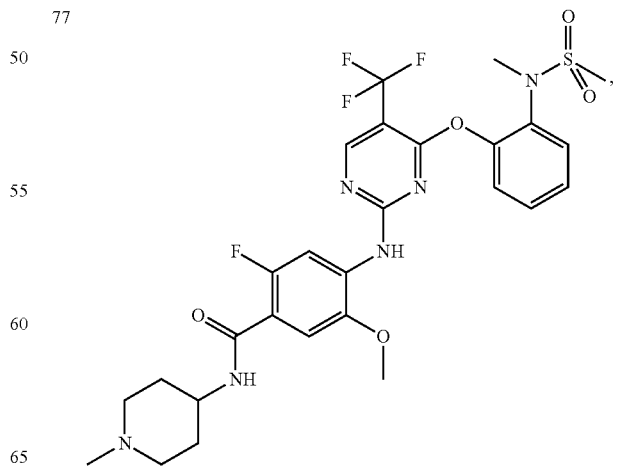

78 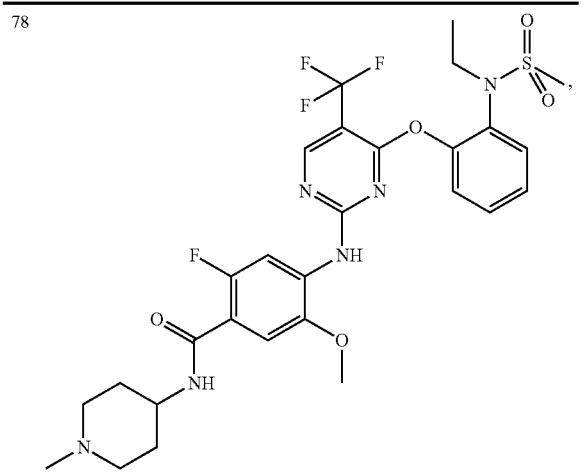

79 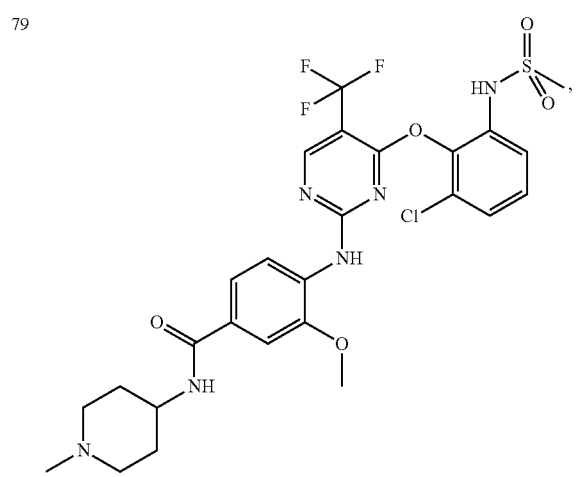

80 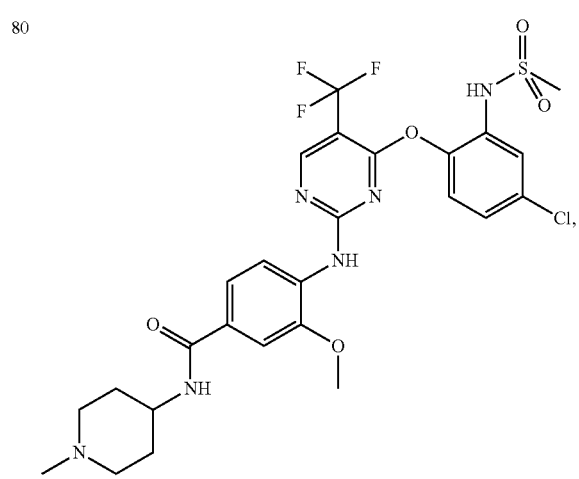

81 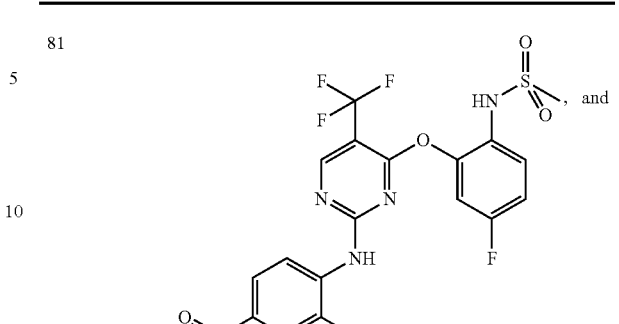

82 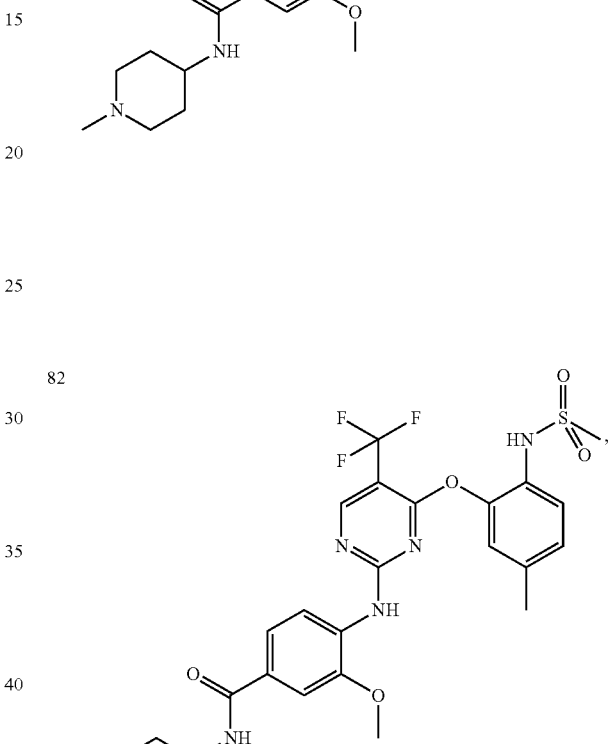

or a pharmaceutically acceptable salt thereof.

2. A pharmaceutical composition comprising a compound according to claim 1 and a pharmaceutically acceptable carrier or diluent.

3. A method for treating prostate carcinoma which comprises administering to a host suffering from such condition a therapeutically effective amount of a compound according to claim 1.

* * * * *